(12) United States Patent
Sherman et al.

(10) Patent No.: US 11,406,776 B2
(45) Date of Patent: Aug. 9, 2022

(54) LIFE SUPPORT AND MONITORING APPARATUS WITH MALFUNCTION CORRECTION GUIDANCE

(71) Applicant: ZOLL Medical Corporation, Chelmsford, MA (US)

(72) Inventors: Leslie H. Sherman, Denville, NJ (US); George Beck, Mendham, NJ (US); Denise Eizadkhah, Bridgewater, NJ (US); Dorian LeCroy, New York, NY (US)

(73) Assignee: ZOLL Medical Corporation, Chelmsford, MA (US)

( * ) Notice: Subject to any disclaimer, the term of this patent is extended or adjusted under 35 U.S.C. 154(b) by 254 days.

(21) Appl. No.: 16/782,578

(22) Filed: Feb. 5, 2020

(65) Prior Publication Data

US 2020/0246566 A1    Aug. 6, 2020

Related U.S. Application Data

(63) Continuation of application No. 15/016,602, filed on Feb. 5, 2016, now Pat. No. 10,589,044, which is a
(Continued)

(51) Int. Cl.
*A61M 16/00* (2006.01)
*A61B 5/00* (2006.01)
(Continued)

(52) U.S. Cl.
CPC ........ *A61M 16/0051* (2013.01); *A61B 5/00* (2013.01); *A61B 5/08* (2013.01); *A61M 16/0069* (2014.02); *A61M 16/024* (2017.08); *A61M 16/101* (2014.02); *A61M 16/0063* (2014.02); *A61M 2016/0021* (2013.01); *A61M 2016/0027* (2013.01); *A61M 2202/0208* (2013.01); *A61M 2205/3303* (2013.01); *A61M 2205/3368* (2013.01); *A61M 2205/502* (2013.01); *A61M 2205/505* (2013.01); *A61M 2205/581* (2013.01); *A61M 2205/583* (2013.01);
(Continued)

(58) Field of Classification Search
CPC .......... A61M 16/0003; A61M 16/0051; A61M 16/1005; A61M 2016/1025; A61M 2205/18; A61M 2205/502; A61M 2205/505; A62B 7/00; A62B 9/006
See application file for complete search history.

(56) References Cited

U.S. PATENT DOCUMENTS 5,103,814 A    4/1992  Maher
5,262,944 A *  11/1993 Weisner ................. G16H 40/63
                                                    600/300
(Continued)

*Primary Examiner* — Valerie L Woodward
(74) *Attorney, Agent, or Firm* — The Webb Law Firm

(57) ABSTRACT

A life support and monitoring apparatus with malfunction correction guidance is provided. The life support and monitoring apparatus of the present disclosure identifies the root cause or potential cause of a fault/failure and then prompts an operator to take appropriate steps to assure the continuance of life support and critical physiologic monitoring. When multiple faults/failures exist, the apparatus automatically prioritizes them based on risk to the patient and prompts the operator to do the most appropriate intervention to assure patient safety.

30 Claims, 8 Drawing Sheets

Related U.S. Application Data continuation of application No. 12/780,095, filed on May 14, 2010, now Pat. No. 9,283,339.

(60) Provisional application No. 61/179,108, filed on May 18, 2009.

(51) Int. Cl.
 *A61B 5/08* (2006.01)
 *A61M 16/10* (2006.01)

(52) U.S. Cl.
 CPC ............... *A61M 2205/8206* (2013.01); *A61M 2230/205* (2013.01); *A61M 2230/432* (2013.01)

(56) References Cited

U.S. PATENT DOCUMENTS

| | | | |
|---|---|---|---|
| 5,317,506 A * | 5/1994 | Coutre | A61M 5/16831 604/65 |
| 5,319,355 A | 6/1994 | Russek | |
| 5,687,717 A * | 11/1997 | Halpern | A61B 5/0205 600/300 |
| 5,881,723 A * | 3/1999 | Wallace | G16H 40/63 128/204.21 |
| 6,369,838 B1 | 4/2002 | Wallace et al. | |
| 6,761,165 B2 | 7/2004 | Strickland, Jr. | |
| 7,527,054 B2 | 5/2009 | Misholi | |
| 7,787,946 B2 | 8/2010 | Stahmann et al. | |
| 9,283,339 B2 | 3/2016 | Sherman et al. | |
| 2003/0062045 A1* | 4/2003 | Woodring | A61M 16/024 128/204.18 |
| 2003/0065308 A1 | 4/2003 | Lebel et al. | |
| 2004/0236240 A1* | 11/2004 | Kraus | G16H 40/63 600/529 |
| 2005/0085799 A1* | 4/2005 | Luria | A61M 16/0009 606/1 |
| 2006/0249151 A1 | 11/2006 | Gambone | |
| 2007/0077200 A1 | 4/2007 | Baker | |
| 2008/0072896 A1 | 3/2008 | Setzer et al. | |
| 2008/0230062 A1 | 9/2008 | Tham | |
| 2009/0090363 A1* | 4/2009 | Niland | A61M 16/122 128/203.26 |
| 2009/0133695 A1 | 5/2009 | Rao et al. | |
| 2009/0212962 A1* | 8/2009 | Chekal | A62B 18/088 340/632 |
| 2009/0241957 A1 | 10/2009 | Baker, Jr. | |
| 2010/0224192 A1* | 9/2010 | Dixon | A61B 5/02416 128/204.23 |

* cited by examiner

SYMBOLS AND ICONS

| Name | Symbol | Description |
|---|---|---|
| OFF | ○ | |
| ON | | | |
| DIRECT CURRENT | === | IDENTIFIES THE LOCATION TO CONNECT EXTERNAL DC POWER |
| MUTE/CANCEL | ⊗ | IDENTIFIES BUTTON WHICH MUTES THE ACTIVE ALARM OR CANCELS THE PARAMETER SELECTION |
| ACCEPT/CONFIRM | ✓ | IDENTIFIES BUTTON WHICH ACCEPTS THE PARAMETER SELECTION |
| ESD | | WARNS THAT CONNECTOR PINS SHOULD NOT BE TOUCHED |
| DEFIBRILLATION PROOF | ⊣🯅⊢ | INDICATES THE DEGREE OF PROTECTION AGAINST ELECTRICAL SHOCK |
| ALARM BELL | 🔔 | IDENTIFIES ALARM LIMITS SETTINGS<br>IDENTIFIES THE ON-SCREEN ALARM |
| ALARM BELL OUTLINE | 🔔 | IDENTIFIES THE NUMBER OF OFF-SCREEN ALARMS |
| ATTENTION WARNING | ⚠!! | HIGH PRIORITY ALARM ACTIVE |
| | ⚠ | MEDIUM PRIORITY ALARM ACTIVE |
| | △ | LOW PRIORITY ALARM ACTIVE |
| MUTE | 🔇 | ACTIVE ALARM AUDIBLE SIGNAL MUTED |
| SPEAKER | 🔊 | ACTIVE ALARM AUDIBLE SIGNAL |
| OXYGEN SUPPLY | | OXYGEN SUPPLY CONNECTED |
| EXTERNAL POWER | 🔌 | INDICATES THE UNIT IS OPERATING USING AN EXTERNAL POWER SOURCE |
| NO EXTERNAL POWER | 🚫🔌 | INDICATES THE UNIT IS OPERATING WITHOUT AN EXTERNAL POWER SOURCE |
| INTERNAL BATTERY | 🔋 | PROVIDES INDICATION OF BATTERY CAPACITY AND CHARGING STATUS |
| NO INTERNAL BATTERY | 🚫🔋 | INDICATES WHEN INTERNAL BATTERY IS NOT AN AVAILABLE POWER SOURCE |
| HEART | ♥ | PROVIDES INDICATION THAT THE PULSE OXIMETER IS IN USE |
| HEART OUTLINE | ♡ | PROVIDES INDICATION THAT AN ACTIVE ALARM IS ASSOCIATED WITH PULSE OXIMETER FUNCTIONALITY |

FIG.6

LIFE SUPPORT AND MONITORING APPARATUS WITH MALFUNCTION CORRECTION GUIDANCE

This application is a continuation application of U.S. application Ser. No. 15/016,602, filed Feb. 5, 2016, which is a continuation application of U.S. application Ser. No. 12/780,095, filed May 14, 2010, now U. S. Pat. No. 9,283,339, which claims priority to U.S. Provisional Application No. 61/179,108, filed May 18, 2009, all of which are incorporated herein by reference in their entirety.

BACKGROUND

1. Field

The present disclosure relates generally to medical systems, and more particularly, to a life support and monitoring apparatus with malfunction correction guidance.

2. Description of the Related Art

Achieving adequate ventilation and oxygenation are the primary goals of life support systems. These goals are accomplished through the regular adjustment of parameters which control the number of breaths, the volume or pressure delivered with each breath, the inspired oxygen concentration ($FIO_2$) and the end-expiratory pressure (PEEP). To manage these parameters, a number of controls provide for discrete adjustment of the gas flow, flow timing, air/oxygen ($O_2$) mixing and airway pressure. Physiologic parameters such as oxyhemoglobin saturation ($SpO_2$), end-tidal $CO_2$ (ETCO2), heart rate, blood pressure and temperature all play a critical role in the management of life support and are either monitored continuously or intermittently to assure homeostasis. A medical attendant is also responsible for maintaining a number of tubes and hoses (collectively known as the breathing circuit) which conduct gas to and from the patient and the physiologic sensors with their cables that attach to the patient for monitoring. Care providers must also monitor and manage the consumable resources (power, oxygen and compressed air, etc). Active monitoring and management of the patient and life support apparatus is typically guided by continuous noninvasive monitoring of oxygen saturation by pulse oximetry ($SpO_2$), continuous sampling of exhaled carbon dioxide ($ETCO_2$) as well as electrocardiogram (ECG), blood pressure (BP) both invasive and noninvasive, and temperature. Intermittent arterial blood sampling to measure arterial oxygen tension ($PaO_2$), carbon dioxide tension ($PaCO_2$), hydrogen ion concentration (pH) and the measured oxygen saturation ($SaO_2$) is also required.

As a result of the inherent complexity of life support and the associated apparatus, care providers are required to constantly monitor and make adjustments to the apparatus to assure an appropriate level of support. Interruptions in care, even for a few breaths, can significantly affect mortality and/or patient recovery. So, when a fault or failure of the apparatus, breathing circuit, supporting resources ($O_2$ supply, power, etc.), physiologic sensors, or patient occurs, the care provider must immediately diagnose and intervene to assure life support is maintained. Conventional life support systems have used alarm systems that detect the fault or failure and indicate the alarm state by identifying whether a parameter or parameters are above or below the acceptable range along with an audible and visible alarm annunciation. The immediate need to respond requires that the care provider have sufficient clinical knowledge, experience with the apparatus in use and the ability to quickly survey the equipment, connections and patient condition to identify any physical disruptions in the life support system. Based on this rapid assessment, the care provider must prioritize their intervention so that patient care and safety are maintained. This alarm approach places the majority of the burden for a successful intervention and safety of the patient on the care provider and their experience.

Therefore, a need exists for automatic non-human techniques to identify causes of fault/failures in a life support and monitoring apparatus and to provide specific guidance and/or instruction on how to mitigate the fault/failure while safely managing the patient and equipment. Use of such techniques will have a broad impact on patient care as appropriate intervention will be less dependent on care provider memory of procedural training and experience.

SUMMARY

A life support and monitoring apparatus with malfunction correction guidance is provided. The life support and monitoring apparatus of the present disclosure identifies the root cause or potential cause of a fault/failure and then prompts an operator to take appropriate steps to assure the continuance of life support and critical physiologic monitoring. When multiple faults/failures exist, the apparatus automatically prioritizes them based on risk to the patient and prompts the operator to do the most appropriate intervention to assure patient safety.

BRIEF DESCRIPTION OF THE DRAWING

The above and other aspects, features, and advantages of the present disclosure will become more apparent in light of the following detailed description when taken in conjunction with the accompanying drawings.

FIG. 6 illustrates the symbols and icons employed with the user interface of the life support and monitoring apparatus of the present disclosure.

Figure 1:
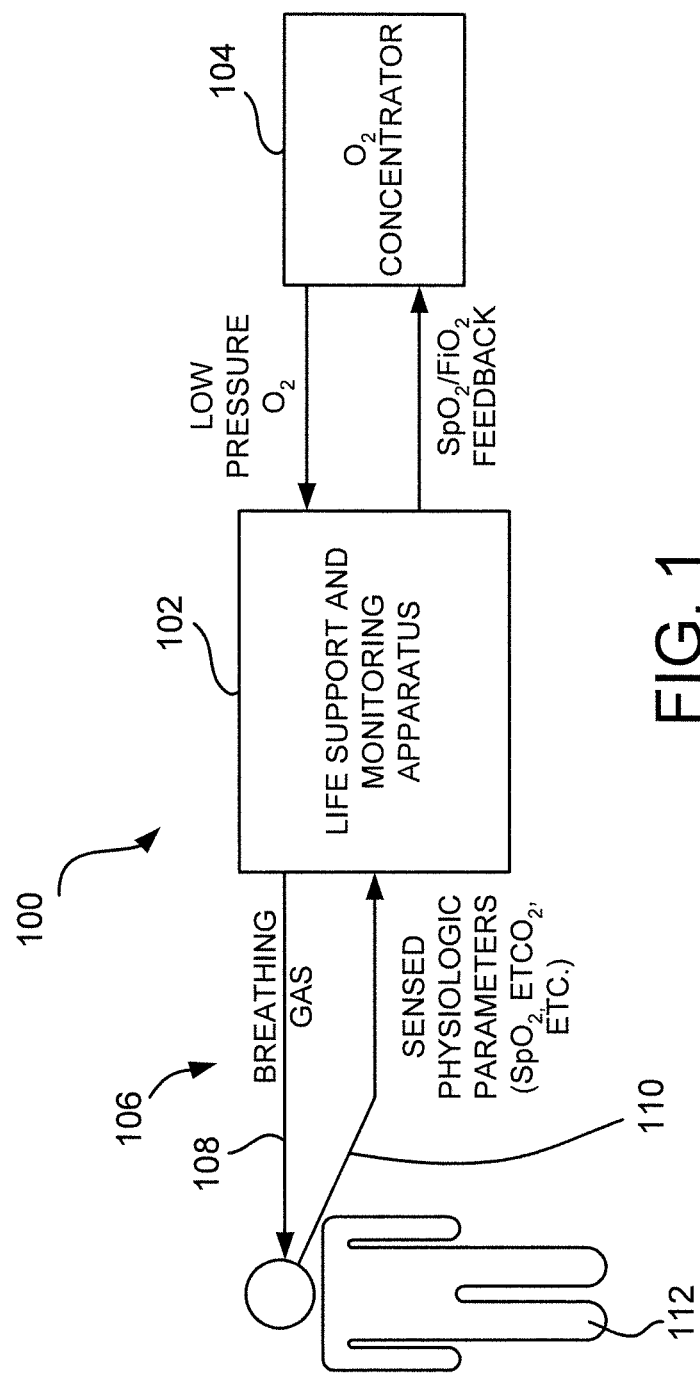
FIG. 1 is a diagram of a life support and monitoring apparatus with oxygen generation capability having closed loop control of FiO2 in accordance with an embodiment of the present disclosure.

To facilitate understanding, the images in the drawings are simplified for illustrative purposes and are not depicted to scale.

The appended drawings illustrate exemplary embodiments of the present disclosure and, as such, should not be considered as limiting the scope of the disclosure that may admit to other equally effective embodiments. Correspondingly, it has been contemplated that features or steps of one embodiment may beneficially be incorporated in other embodiments without further recitation.

In some embodiments, particular method steps of the discussed methods are performed in the depicted order. In alternate embodiments, in the respective methods, at least two method steps or portions thereof may be performed contemporaneously, in parallel, or in a different order.

DETAILED DESCRIPTION

The present description illustrates the principles of the present disclosure. It will thus be appreciated that those skilled in the art will be able to devise various arrangements that, although not explicitly described or shown herein, embody the principles of the disclosure and are included within its spirit and scope.

All examples and conditional language recited herein are intended for pedagogical purposes to aid the reader in understanding the principles of the disclosure and the concepts contributed by the inventor to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Thus, for example, it will be appreciated by those skilled in the art that the block diagrams presented herein represent conceptual views of illustrative circuitry embodying the principles of the disclosure. Similarly, it will be appreciated that any flow charts, flow diagrams, state transition diagrams, pseudo-code, and the like represent various processes which may be substantially represented in computer readable media and so executed by a computer or processor, whether or not such computer or processor is explicitly shown.

The functions of the various elements shown in the figures may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor ("DSP") hardware, read only memory ("ROM") for storing software, random access memory ("RAM"), and nonvolatile storage, programmable logic or other device or devices.

Other hardware, conventional and/or custom, may also be included. Similarly, any switches shown in the figures are conceptual only. Their function may be carried out through the operation of program logic, through dedicated logic, through the interaction of program control and dedicated logic, or even manually, the particular technique being selectable by the implementer as more specifically understood from the context.

The word "exemplary" is used herein to mean "serving as an example, instance, or illustration." Any configuration or design described herein as "exemplary" is not necessarily to be construed as preferred or advantageous over other configurations or designs. Herein, the phrase "coupled with" is defined to mean directly connected to or indirectly connected with through one or more intermediate components. Such intermediate components may include both hardware and software based components.

Referring to FIG. 1, a life support and monitoring apparatus 100 having malfunction correction guidance is provided. The apparatus 100 includes a ventilator and physiologic monitoring module 102 for life support (e.g., supplying mechanical ventilation, supplemental $O_2$ and critical care monitoring) of a patient using an $O_2$ concentrator 104 coupled to the ventilator module 102 for supplying $O_2$ to the ventilator module in the apparatus 100. The apparatus 100 further includes a patient breathing circuit 106 which includes supply tubes and a hose 108 for supplying breathing gas (e.g., air or some combination of air and $O_2$) to the patient 112 and return connections 110 for sending sensed or measured physiologic data signals from the patient to the life support and monitoring apparatus 102.

Figure 2:
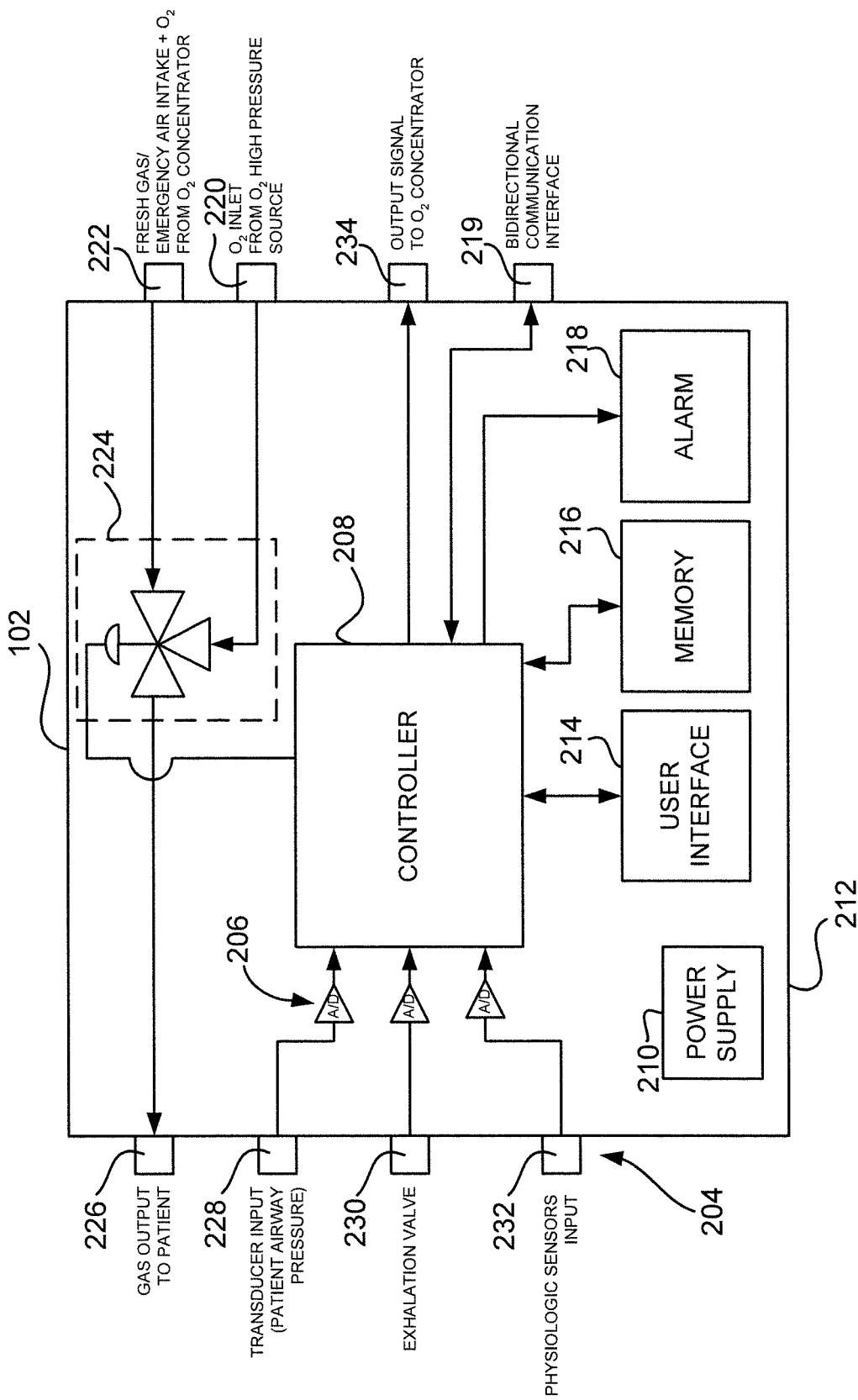
FIG. 2 is a block diagram of a life support and monitoring apparatus in accordance with an embodiment of the present disclosure.

FIG. 2 illustrates a block diagram of the life support and monitoring apparatus 102. Generally, the apparatus 102 includes input connections for a plurality of sensors 204, a plurality of analog-to-digital (A/D) converters 206 reside in the apparatus or are part of the sensor modules contained within the apparatus for converting the inputted sensors into digital form and a controller 208 controlling an output of the apparatus 102 based on the sensed parameters of the inputs. In one embodiment, the controller 208 will include a central processing unit (CPU) and/or a digital signal processor (DSP). The controller 208 is configured for receiving the digital signals from the A/D converters 206 to perform the necessary calculations for controlling the overall operations of the apparatus 102.

A power supply 210 is also provided for providing power to components of the apparatus 102. In one embodiment, the power supply 210 is coupled to an external power source, e.g., 120V power source. In another embodiment, the power supply 210 is coupled to an internal rechargeable battery integrated in the housing 212 of the apparatus 102.

The life support and monitoring apparatus 102 of the present disclosure includes a user interface 216 for interacting with a user and for communicating events, alarms and instructions to the user. The user interface includes a display for providing visual indications to the user and a plurality of inputs or controls disposed on the housing for inputting information to the apparatus 102. The display may include a touch screen, a liquid crystal display (LCD), a plurality of LED number segments, individual light bulbs or any combination of these. The display may provide the information to the user in the form of alpha-numeric lines, computer-generated graphics, videos, etc. Visual information provided on the display may include but is not limited to instructional videos, operating manuals associated with the ventilator, a flowchart for troubleshooting, a checklist for troubleshooting, etc. Digital files including the various visual instructions are stored in either memory 216 or retrieved from a remote event server.

The user interface 216 will also include an audible output device, e.g., a speaker. The speaker will be coupled to the controller 208 via a digital-to-analog converter (D/A) for converting digital audio files stored in memory 216 to analog signals playable by the speaker. The audible output device may simply provide audible instructions to a user when an event is detected or may provide audio with a corresponding video being displayed on the display.

The life support and monitoring apparatus 102 of the present disclosure will support various file types including but not limited to Microsoft Windows Media Video files (.wmv), Microsoft Photo Story files (.asf), Microsoft Windows Media Audio files (.wma), MP3 audio files (.mp3), JPEG image files (.jpg, .jpeg, .jpe, .jfif), MPEG movie files (.mpeg, .mpg, .mpe, .m1v, .mp2v .mpeg2), Microsoft Recorded TV Show files (.dvr-ms), Microsoft Windows Video files (.avi) and Microsoft Windows Audio files (.wav).

The memory 216 is configured for storing files executable by the controller, files associated with the visual and/or audible instructions and patient data collected from the life support and monitoring modules. The memory 216 includes internal storage memory, e.g., random access memory (RAM), or removable memory such as magnetic storage memory; optical storage memory, e.g., the various known types of CD and DVD media; solid-state storage memory, e.g., a CompactFlash card, a Memory Stick, SmartMedia card, MultiMediaCard (MMC), SD (Secure Digital) memory; or any other memory storage that exists currently or will exist in the future. By utilizing removable memory, the apparatus 102 can be easily upgraded with new instruction files as needed.

In one embodiment, the digital audio files may be programmed directly through the apparatus 102. In this embodiment, the apparatus 102 will include an audio input device, e.g., a microphone, for receiving spoken words in the form of analog signals. The analog signals will then be sent to an analog-to-digital converter (A/D) to convert the analog signals into digital signals understandable by the controller 208. The controller 208 will then store the recorded digital audio file in the memory 216 or use the signals to control the device by hands-free voice control. The user may associate the recorded digital file with a particular alarm through the touch screen display. Alternatively, the user may associate the recorded digital file with an event code.

In a further embodiment, the life support and monitoring apparatus 102 will include an alarm module 218 to provide audible and visible alarm messaging separate from the user interface 214 for indicating alarms to a remote user.

The life support and monitoring apparatus 102 also includes a bidirectional communication interface 219 that provides for remote control and monitoring of the device using a wired communication system. In a further embodiment, the bidirectional communication interface 219 of the apparatus 102 will provide wireless command and control allowing remote clinicians to monitor and manage care.

The life support and monitoring apparatus 102 includes an $O_2$ inlet 220 for receiving $O_2$ from an $O_2$ concentrator or high-pressure $O_2$ source 104 and a fresh gas/emergency air intake 222 which are all piped to a 3-way mixing valve/ventilator module 224. The fresh gas/emergency air intake 222 allows ambient air into the ventilator module 102 internal compressor and also functions as an internal antiasphyxia valve which allows the patient to breathe ambient air in the event of a ventilator module failure. The controller 208 will modulate the mixing valve/ventilator module 224 to achieve a determined level of $FIO_2$ which will be supplied to a patient via gas output 226. The controller 208 will determine the proper level of $FIO_2$ based on the input sensors 204, e.g., transducer input 228, exhalation valve input 230 and physiologic sensors input 232. It is to be appreciated that there can be any number of physiologic sensor inputs, e.g., $SpO_2$, ETCO2 input, a heart rate input, blood pressure input, temperature input, etc. An output port 234, e.g., a USB port, is provided to communicate to and control the $O_2$ concentrator 104.

The apparatus 100 provides a suite of alarms to alert the operator when conditions exceed parameter limits or when operation is affected by a patient, external and/or internal fault or failure. When an alarm occurs, the operator is alerted by audible and visual indicators while context sensitive help messages are displayed on the face of the housing of the apparatus.

Figure 3A:
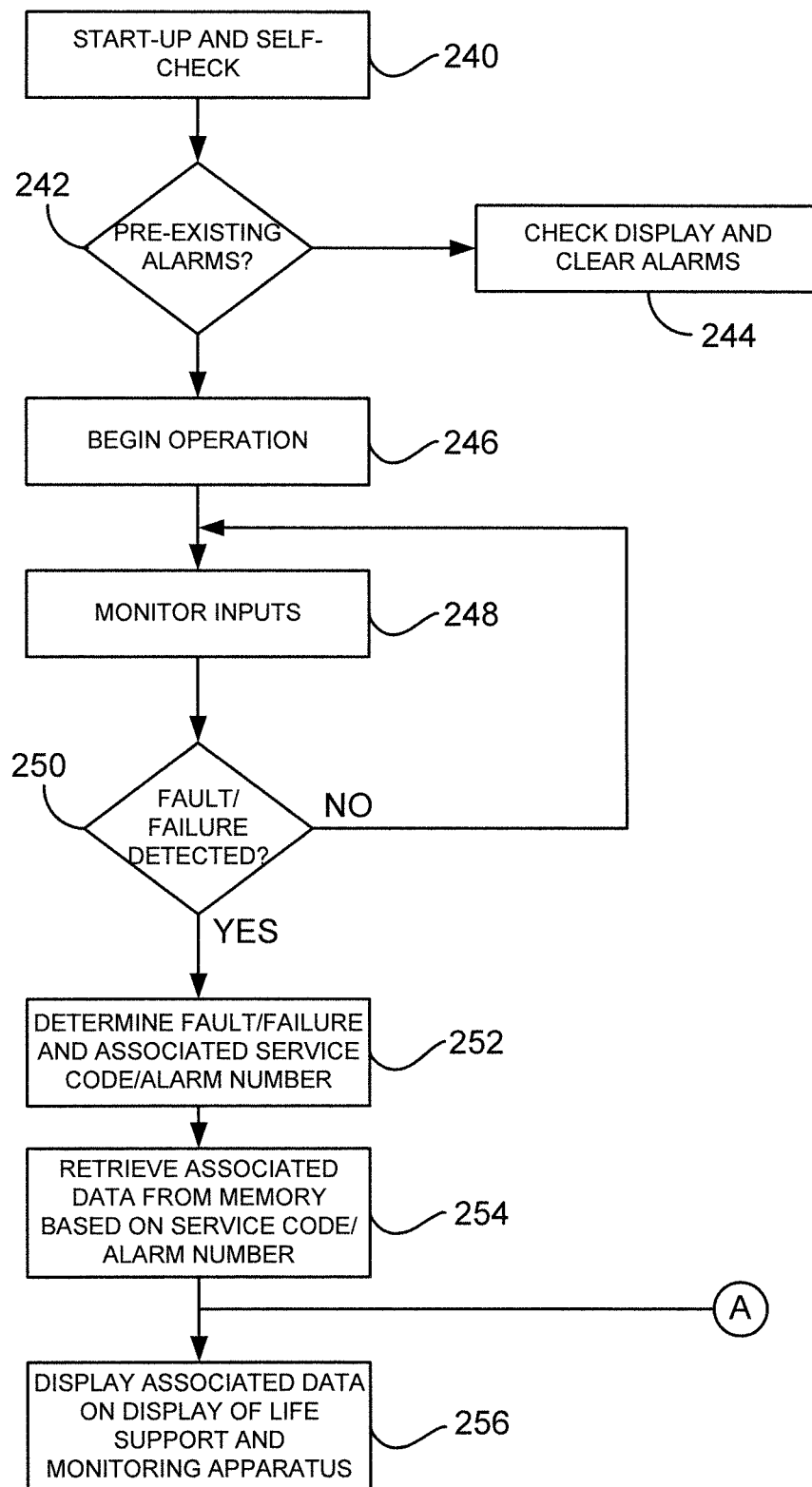
FIGS. 3A-B illustrate a flow diagram of an exemplary method for providing malfunction correction guidance of a life support and monitoring apparatus in accordance with an embodiment of the present disclosure.

FIG. 3A is a flow diagram of an exemplary method for providing malfunction correction guidance of a life support and monitoring apparatus, e.g., a ventilator, in accordance with an embodiment of the present disclosure. Initially, the apparatus 102 will start-up and perform a self-test to ensure all subsystems are collectively working properly, step 240. At step 242, the controller 208 determines if there are any preexisting alarms. If there are preexisting alarms, the controller 208 will cause the display of the user interface 214 to display the alarm(s) and provide instructions on how to resolve the fault/failure, step 244. Otherwise, at step 246, the ventilator 102 will begin operation and continuously monitor the inputs to the ventilator 102, step 250.

At step 250, the controller 208 of the apparatus 102 will determine if any fault/failure has occurred. If the controller 208 has determined a fault/failure has occurred, the controller 208 determines the fault/failure and its associated service code/alarm number, step 252. The controller 208 then retrieves associated data from the memory 216 based on the determined service code/alarm number, step 254. The controller 208 then causes the display of the user interface 214 to display the associated data. As will be described in more detail below, the associated data will include at least an alarm name and description, mitigation/resolution instructions, if not resolved instructions and an indication of the priority of the alarm.

Figure 3B:
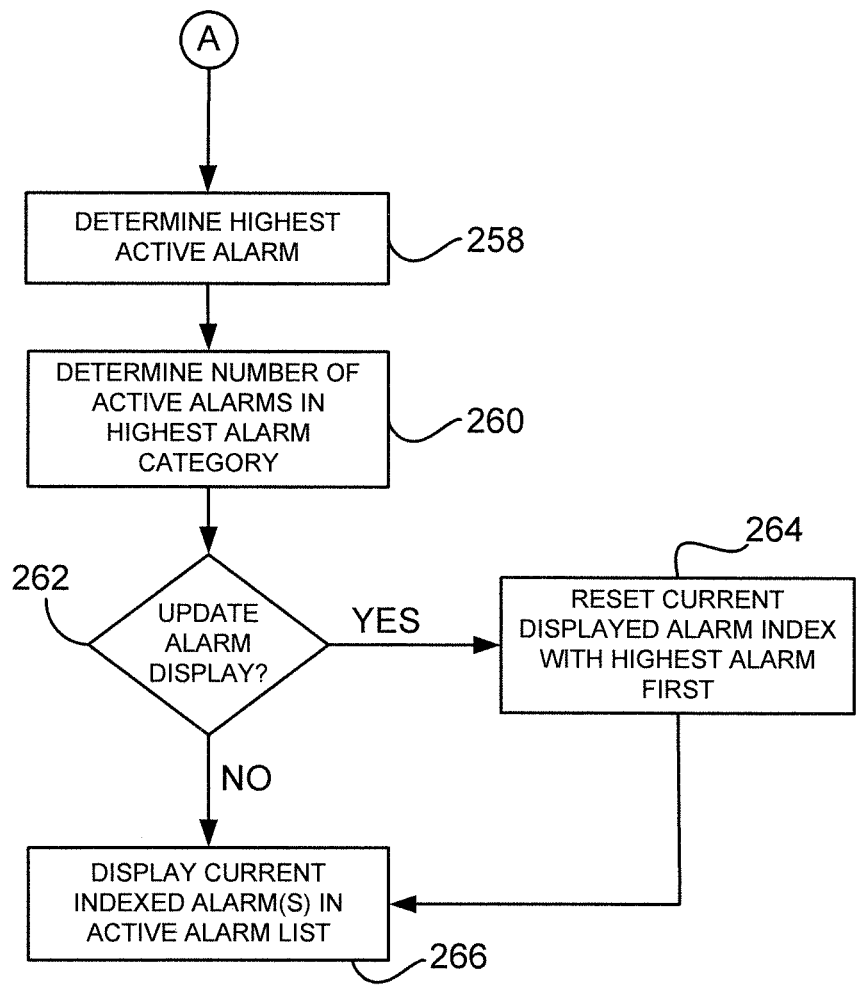

In a further embodiment, when multiple faults/failures exist, the apparatus automatically prioritizes them based on risk to the patient and prompts the operator to do the most appropriate intervention to assure patient safety. Referring to FIG. 3B, the apparatus 102 will process the alarm or event as described above up to step 254. If multiple alarms or events are active, the controller 208 will determine the highest active alarm category, in step 258. Next, in step 260, the controller 208 will determine a number of active alarms in the highest alarm category. The controller 208 will determine if the display needs to be updated based on the determined priorities of the active alarms, step 262. If the display needs to be updated, the controller 208 will reset the current displayed alarm index with the highest alarm first (step 264), i.e., the alarm with the highest priority. Otherwise, the controller 208 will display the current indexed alarm(s) in the active alarm list (step 266).

In one embodiment, if multiple alarms or events are indexed and listed on the display, the operator may select the desired alarm to view the context-based mitigation instructions. In another embodiment, the prioritized alarms must be handled in a predetermined order. For example, the controller 208 will lock out the operator from viewing a lower priority alarm until the highest priority alarm is rectified.

Figure 4:
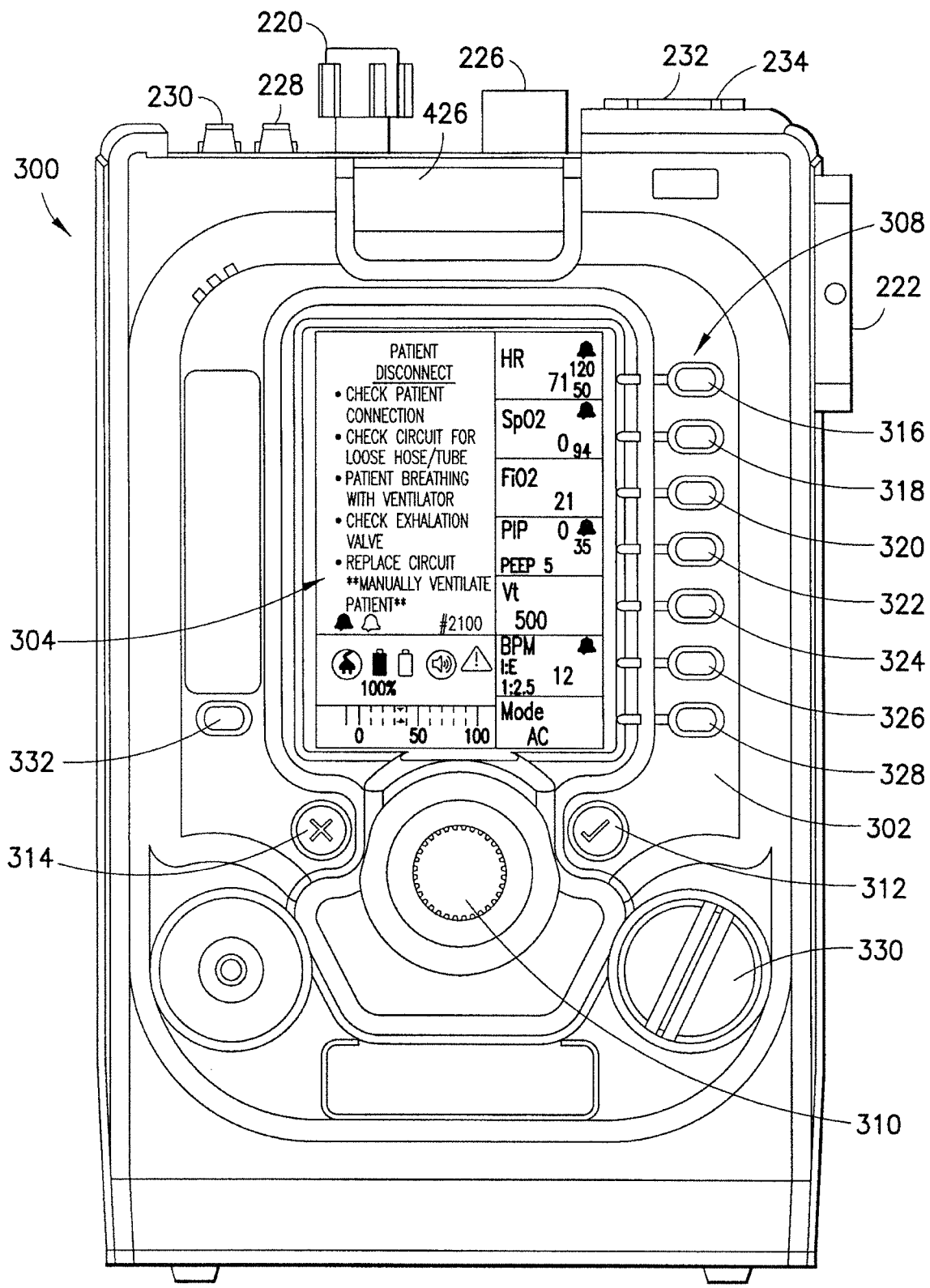
FIG. 4 is an exemplary configuration of a life support and monitoring apparatus in accordance with an embodiment of the present disclosure.

Referring to FIG. 4, an exemplary configuration of a ventilator 300 in accordance with the teachings of the present disclosure is shown. The ventilator 300 includes various controls, indicators and connections. Their placement has been chosen to facilitate ease of use and visibility in all operating environments. The connections are labeled to correspond to the connections shown and described in FIG. 2. Control panel 302 incorporates all controls and a liquid crystal display (LCD) display 304. The LCD display 304 provides continuous display of control settings, operating conditions, power, and alarm status information.

The core concept for operating all major functions of the apparatus 300 is by pressing a PARAMETER button 308 associated with the parameter an operator wishes to change. Pressing the PARAMETER button 308 highlights the primary parameter followed by the secondary parameters moving in a clockwise direction. When the desired parameter is highlighted, the operator turns the ROTARY ENCODER 310 clockwise or counter clockwise to adjust the parameter to the desired value. The operator then confirms that they want to operate with this new value by pressing the CONFIRM/SELECT button 312. Once this is done the highlight goes away and the unit begins operation using the new parameter. At any point, the operator may cancel any operation and return to the primary operating screen by pressing the MUTE/CANCEL button 314. When a parameter is selected (highlighted), it stays active for 5 seconds; after this time the unit automatically cancels the operation and returns to the default screen.

Each control will now be described with reference to FIG. 4.

HR (316)—Pressing the HR button 316 will highlight the current value of the High Heart Rate Alarm Limit and enable its value to be changed. Pressing the HR button a second time will highlight the current value of the Low Heart Rate Alarm Limit and enable its value to be changed. The HR parameters are functional only when the pulse oximeter is connected. Both limits are adjustable in 1 b/min increments. The default value at start up for the high alarm limit is 120 b/min; the low alarm limit is 40 b/min.

SpO$_2$ (318)—Pressing the SpO$_2$ button 318 will highlight the current Low SpO$_2$ Alarm Limit value. The SpO$_2$ display is active only when the pulse oximeter is connected. When no SpO$_2$ sensor is connected during start up or the operator turns off the pulse oximeter, "off" is displayed in the parameter window. The default value at start up is 94%.

FlO$_2$ (320)—pressing the FlO$_2$ button 320 will highlight the current FlO$_2$ setting. The default value at start up is 21%.

PIP (PEAK INSPIRATORY PRESSURE) (322)—pressing the PEAK INSPIRATORY PRESSURE button 322 will highlight the high airway pressure alarm limit. The high alarm limit default value at start up is 35 cm H$_2$O. Alarm values greater than 60 cm H$_2$O require the user to perform a separate confirmation to assure the value is required to manage the particular patient.

Vt (TIDAL VOLUME) (324)—pressing the TIDAL VOLUME button 324 will highlight the current value and enable its current value to be changed. The default value at start up is 500 ml.

BPM (BREATHING RATE) (326)—pressing the BPM button 326 highlights the current value. The I:E ratio is also displayed in this window but cannot be changed by the operator. The default BPM value at start up is 12 BPM.

MODE (328)—Pressing the MODE button 328 allows the operator to select the mode of mechanical ventilation. The current embodiment provides for assist control (AC), synchronized intermittent mandatory ventilation (SIMV) and continuous positive airway pressure (CPAP) modes of ventilation with both volume and pressure breath targeting.

CONFIRM/SELECT (312)—press the CONFIRM/SELECT button 312 to confirm a new control setting or to select from a menu or setting option. The CONFIRM/SELECT button switch is labeled with a check green "√".

POWER OFF/ON (330)—turn the POWER OFF/ON switch 330 to apply or remove operating power to the EMV.

ROTARY ENCODER (310)—turn the ROTARY ENCODER 310 clockwise or counter clockwise to change a value or highlight a particular menu option.

ALARM MUTE/CANCEL (314)—press the MUTE/CANCEL pushbutton 314 to mute most Medium Priority Alarms, to cancel/acknowledge Low Priority Alarm or to cancel an action that is no longer desired (for example a control setting change). The MUTE/CANCEL pushbutton switch is labeled with a red "X".

MENU (332)—pressing the MENU pushbutton 332 permits access to user menus and special functions. These may include: (1) Unit Info (Information): lists the serial number for the unit and critical subassemblies, software version, hours of use and last calibration date; (2) Trigger Level: allows the operator to adjust the assisted breath trigger from −6 to −1 cm H$_2$O to optimize patient/ventilator interaction; the default value is −2 cm H$_2$O below baseline; (3) Pulse Oximeter: allows the operator to turn the pulse oximeter on and off; (4) Power Up Settings: allows the operator to select startup settings different from the factory default settings; (5) Storage Mode Menu: allows the operator to configure storage mode to maximize available power or battery life; and (6) Contrast: allows the operator to adjust the contrast of the LCD to optimize visibility in the current lighting environment.

Figure 5:
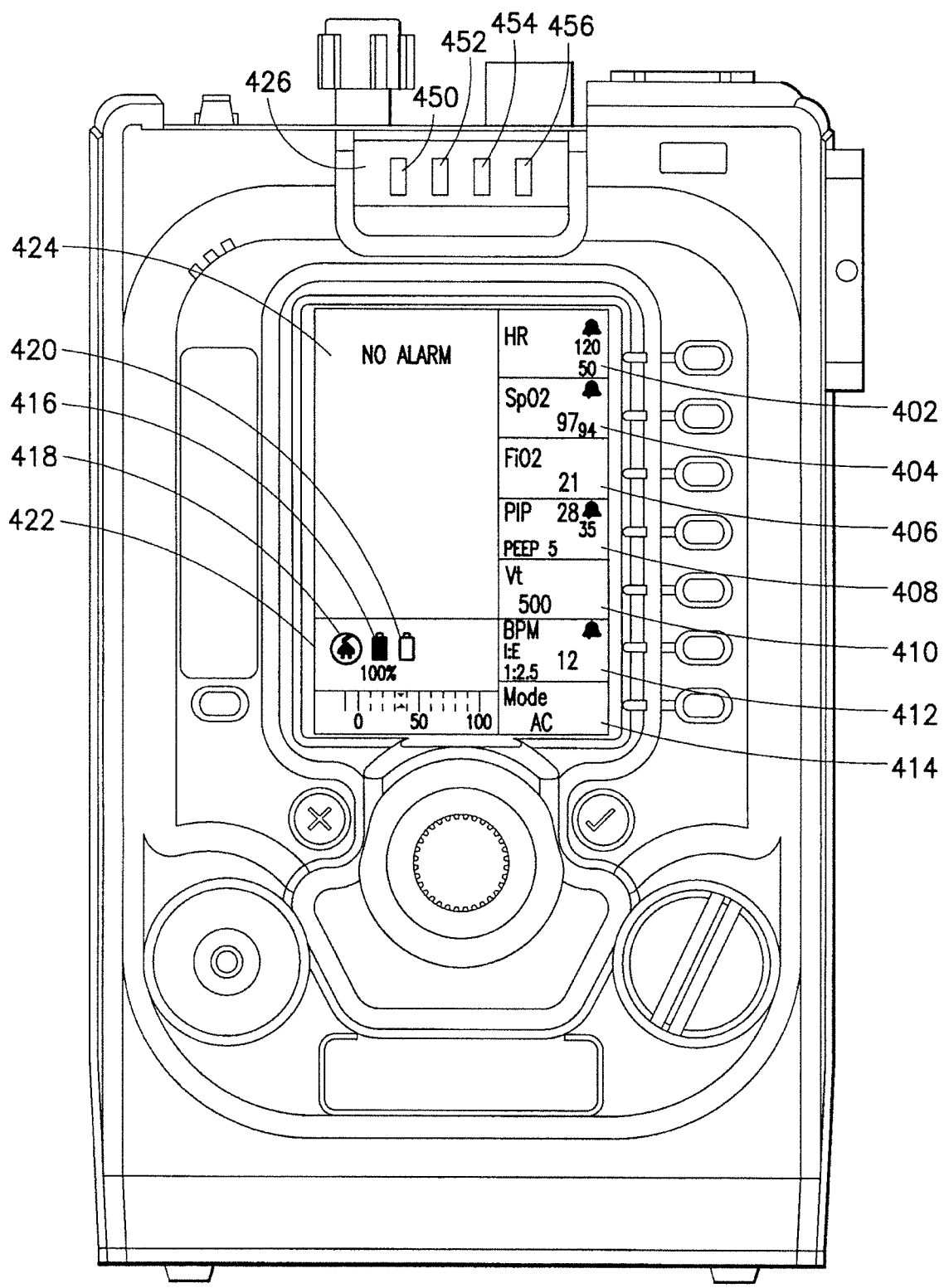
FIG. 5 illustrates the visual indications of a user interface of the life support and monitoring apparatus shown in FIG. 4.

Referring to FIG. 5 of the exemplary apparatus, the visual indicators displayed on display 304 are shown. The LCD parameter windows present information relating to settings, menus/instructions, alarm information, pressure measurement data, pulse oximeter data, and heart rate data. When a parameter, secondary parameter or alarm limit is associated with an active alarm, the parameter flashes to help the operator better understand the nature of the alarm condition. Each of the visual indicators will now be described in relation to FIG. 5, where FIG. 6 illustrates symbols and icons employed.

HR window (402) displays the HR and Low/High HR alarm limits. A heart icon is also displayed in this window when the pulse oximeter is in use. The icon flashes at the patient's heart rate. SpO$_2$ window (404) displays the SpO$_2$ value and the Low SpO$_2$ alarm limit. FlO$_2$ window (406) displays the set fraction of inspired O$_2$. The peak inspiratory pressure (PIP) window (408) displays the peak airway pressure, positive end-expiratory pressure (PEEP) and High PIP alarm limit. The tidal volume (VT) window (410) displays the set tidal volume. BPM window (412) displays the set breath rate and the inspiratory:expiratory (I:E) ratio. MODE window (414) displays the operating mode.

BATTERY Icon/Indicator (416) indicates (1) the presence of a functional battery, (2) when the battery is charging and (3) the current battery capacity. The BATTERY icon appears in outline form and is filled with vertical rows of lines indicating its current capacity. When the battery is charging, these vertical lines cyclically scroll vertically, one row at a time, from the bottom row to the row that corresponds with the current level of charge. When the battery is fully charged, the icon 416 is completely filled with lines and scrolling stops. Each line represents approximately 10% of battery capacity. During internal battery operation, a vertical row "disappears" when battery capacity is reduced by a 10% increment. The BATTERY icon 416 will flash off/on when a Battery Power Low Alarm occurs. The icon 416 will flash off/on and present with a diagonal line when no battery is connected.

EXTERNAL POWER Icon/Indicator 418 indicates the presence of external power. When no external power is detected, the icon/indicator presents with a diagonal line. When an External Power Low or External Power Fail/Disconnect Alarm occurs, the icon flashes off/on.

OXYGEN SUPPLY Icon/Indicator 420 indicates the presence of external $O_2$ (55 psig source). The icon 420 only appears when external oxygen is detected by the pressure transducer. The icon 420 flashes off/on when the Oxygen Low/Fail Alarm occurs.

AIRWAY PRESSURE Graphic 422 provides a continuous display of airway pressure. Its absolute range is from −0 to 100 cm $H_2O$ ATPD with a horizontal resolution of 1 cm $H_2O$/pixel. The scale below the indicator is graduated in 10 cm $H_2O$ increments with numerical markers appearing at 0, 50 and 100 cm $H_2O$.

ALARM MESSAGE CENTER (AMC) 424 is a dedicated area located in the upper left-hand corner of the LCD display 304. At the onset of an alarm, the AMC 424 displays the alarm name and then a series of context-sensitive help messages. These messages serve to guide the operator by presenting suggestions as to the cause and resolution of a particular alarm. When no alarm is present, the AMC displays "No Alarm".

STATUS INDICATOR LED ARRAY 426 contains green 450, yellow 452, red 454 and infrared (IR) 456 LED's. During normal operation the STATUS INDICATOR LED ARRAY is enabled. The LED array illuminates green to indicate the presence of operating power and that all ventilator and patient parameters are within normal limits. A yellow indication by the LED array identifies a low priority alarm indicating that there is information about the device or patient that may require operator attention. Furthermore, the LED array illuminates yellow to indicate the presence of a persistent alarm condition, an operator-acknowledged low priority alarm that has not been resolved. The LED array illuminates red to indicate the presence of High and Medium Priority alarm conditions which require immediate intervention by the operator. The infrared LED is disabled during normal operation and enabled only in the "dark" operating mode. It is visible only to those wearing night vision goggles (NVG'S).

Figure 7:
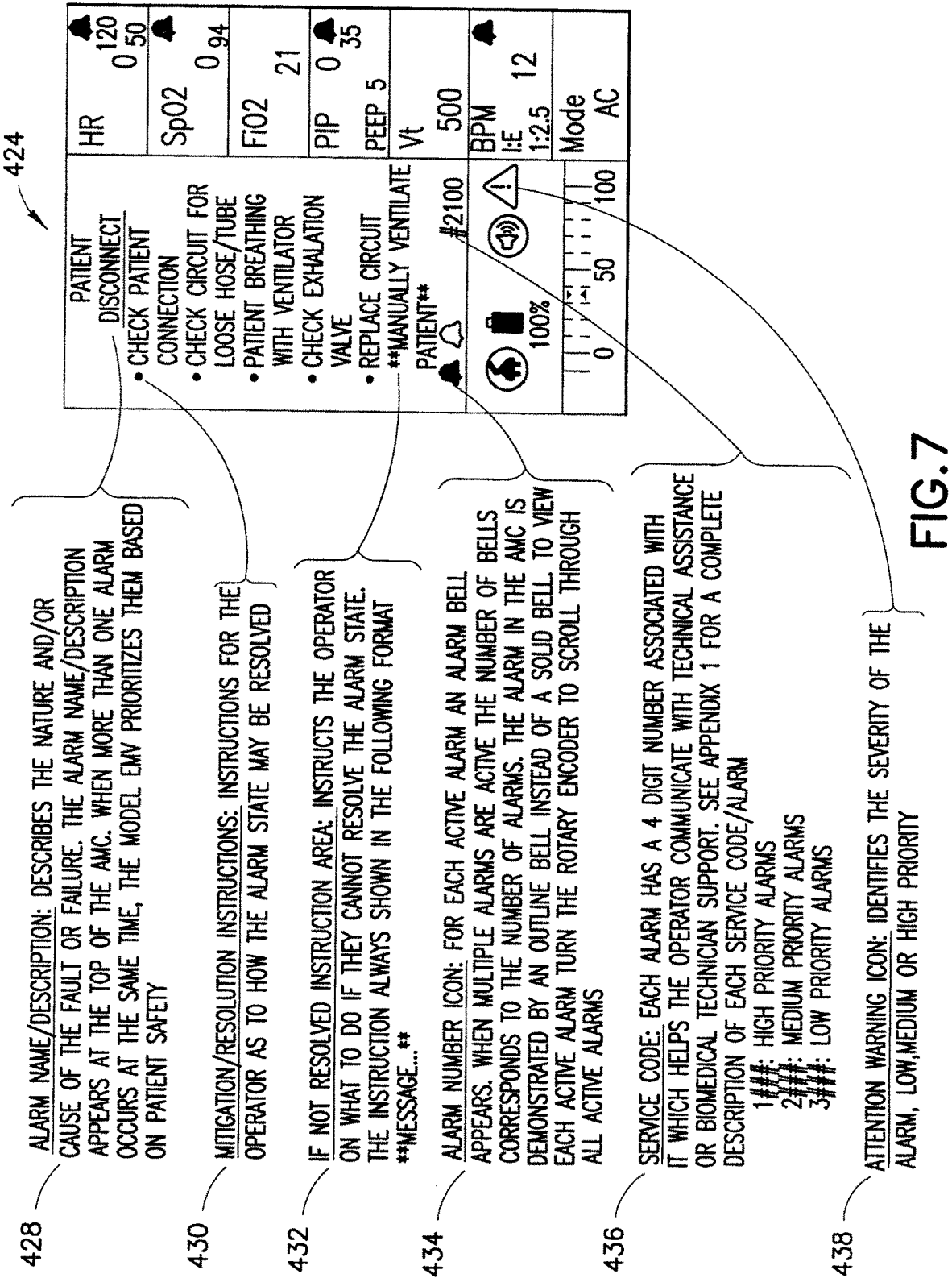
FIG. 7 is an exemplary screen illustrating malfunction correction guidance in accordance with an embodiment of the present disclosure.

The exemplary apparatus 300 use a comprehensive suite of alarms to alert the operator and guide their actions to resolve alarm conditions and assure patient safety. The primary alarm message is displayed at the top of the AMC 424 while guidance and operator instructions are displayed below the alarm name. When multiple alarms occur, they are prioritized and displayed based on the risk to the patient. A complete description of each alarm and how the exemplary apparatus 300 controls alarm conditions will be described below in relation to FIGS. 7 and 8.

At the onset of an alarm, a multi-line message appears in the ALARM MESSAGE CENTER (AMC) 424. The AMC 424 displays the alarm name with a series of messages to help the user resolve the alarm. The number of active alarms is indicated at the bottom of the AMC as a series of ALARM BELL icons with each bell indicating an active alarm. These messages are context-based and suggest what is causing the fault/failure and/or how it can be resolved. The AMC 424 presents alarm messages using the following format:

Alarm Name/Description 428 describes the nature and/or cause of the fault or failure. The Alarm Name/Description 428 appears at the top of the AMC 424. When more than one alarm occurs at the same time, the ventilator 300 prioritizes them based on patient safety. Mitigation/Resolution Instructions 430 provide instructions for the operator as to how the alarm state may be resolved. The If Not Resolved instruction area 432 prompts the operator on what to do if they cannot resolve the alarm state. The instruction 432 is always shown in the following format \*\* Message . . . \*\*.

When multiple alarms are active, the number of alarm bell icons corresponds to the number of active alarms. The alarm shown on the AMC 424 is illustrated by a solid bell. An outlined bell instead of a solid bell illustrates that other off-screen alarms. To view each active alarm, the operator turns the rotary encoder 310 to scroll through all active alarms.

The Service Code 436 for each alarm is displayed in the lower right hand corner of the AMC 424. Each alarm is associated with a 4 digit number which helps the operator communicate with technical assistance or biomedical technician support. The TABLE reproduced at the end of this specification provides a listing of exemplary alarms including the alarm's service code, alarm description and mitigation information. Each service code uses the following format: 1 ###: high priority alarms; 2 ###: medium priority alarms; and 3 ###: low priority alarms.

The Attention Warning Icon 438 identifies the severity of the alarm, low, medium or high priority. Alarm priorities define the operational state of the device regarding its ability to provide mechanical ventilation. Each of the three priorities is described below.

High Priority: mechanical ventilation under operator control is no longer possible. This alarm category requires immediate intervention by the operator. It also includes system failure alarms where the CPU has failed and a backup has taken over to sound the audible and visual alarms and when the device is turned on and there is no internal or external power source. Pressing the Mute/Cancel pushbutton has no affect on the high priority alarm. The alarm can only be silenced by turning off the apparatus.

Medium Priority: mechanical ventilation is active or is possible (maybe for a finite period of time) but there is a failure/fault with the patient, ventilator circuit, a pneumatic subsystem or pulse oximeter. This alarm category requires immediate intervention by the operator. Pressing the Mute/Cancel pushbutton mutes the medium priority alarm for a fixed period between 30 and 120 seconds.

Low Priority: safe mechanical ventilation is active but, there is a fault that the operator must be aware of to assure safe management of the patient and/or ventilator. Low priority alarms present with both an audible and yellow LED alarm signal alerting the user to the condition. Pressing the Mute/Cancel pushbutton cancels the audible signal. If the alarm is not resolved, the yellow LED remains illuminated to remind the operator of the fault or failure.

Alarms are presented and grouped as categories rather than individual alarms because any given fault/failure may have a different affect on patient safety based on what operating resources are available (e.g., external $O_2$, external power, etc.), environmental conditions and the severity of the fault/failure. In each case, the apparatus 300 analyzes the fault/failure and attempts to continue supporting the patient while guiding the operator to make an appropriate intervention to resolve the condition. For example, the controller 208 will determine a fault/failure based on the sensed parameters, e.g., patient airway pressure via transducer input 228, pulse oximeter input 232, etc. Once the fault/failure is determined, the controller 208 determines the service code/alarm number, retrieves the associated record from memory 216 and displays the associated information on display 304. For example, referring to FIG. 7, the controller 208 determines that a patient disconnect has occurred. The controller determines that the service code/alarm number is #2100 and retrieves the associated information from the memory 216. The associated information will be the parameters and instructions displayed on the display 304. In this example, the alarm name/description 428 is "Patient Disconnect". The mitigation/resolution instructions 430 provide five steps or items for the operator to perform in an attempt to rectify the problem. The If Not Resolved Instruction Area 432 instructs the operator to manually ventilate the patient if the mitigation instructions do not resolve the problem. In this example, the service code/alarm number 436 is displayed along with the Attention Warning Icon 438 which in this case signifies a medium priority alarm.

Although the disclosure herein has been described with reference to particular illustrative embodiments, it is to be understood that these embodiments are merely illustrative of the principles and applications of the present disclosure. Therefore numerous modifications may be made to the illustrative embodiments and other arrangements may be devised without departing from the spirit and scope of the present disclosure, which is defined by the appended claims.

Furthermore, although the foregoing text sets forth a detailed description of numerous embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

TABLE

| Service Code | Alarm Name |
|---|---|
| | Alarm description and mitigation information. |
| 1001 | Compressor Failure (Compressor Control Fault - No Backup) |
| | Alarm occurs when the compressor fails to operate or fails to provide the flow required to deliver a breath and high-pressure $O_2$ (HP $O_2$) is not available to provide ventilation. |
| | Mitigation/Info: Manually Ventilate Patient, Connect HP $O_2$, Restart Ventilator With HP $O_2$ |
| | Replace/Service Ventilator |
| 1002 | Compressor Failure (Compressor Signal Chain Fault - No Backup) |
| | Alarm occurs when communication between the compressor controller and Smart Pneumatic Module (SPM) is lost and high-pressure $O_2$ (HP $O_2$) is not available to provide ventilation. |
| | Mitigation/Info: Manually Ventilate Patient, Connect HP $O_2$, Restart Ventilator With HP $O_2$ |
| | Replace/Service Ventilator |
| 1003 | Self Check Failure |
| | Alarm occurs when the flow from the first breath is ±20% of the expected flow for the tidal volume at start up. |
| | Mitigation/Info: Manually Ventilate Patient |
| | Replace/Service Ventilator |
| 1010 | O2 Valve Failure (O2 Valve Failed Open) |
| | Alarm occurs when the $O_2$ valve fails in the open position which results in continuous inspiratory flow. When this occurs the unit automatically opens the exhalation valve to prevent pressure from accumulating in the circuit and ventilation stops. |
| | Mitigation/Info: Manually Ventilate Patient |
| | Replace/Service Ventilator |
| 1011 | O2 Valve Failure (02 Valve Control Fault - No Back Up) |
| | Alarm occurs when the signal to the $O_2$ valve is not delivering the required flow rate and the compressor is not available to provide ventilation. |
| | Mitigation/Info: Manually Ventilate Patient |
| | Replace/Service Ventilator |
| 1012 | O2 Valve Failure (O2 Valve Signal Chain Fault - No Backup) |
| | Alarm occurs when the communication between the $O_2$ valve and the SPM fails and the compressor is not available to provide ventilation. |
| | Mitigation/Info: Manually Ventilate Patient |
| | Replace/Service Ventilator |
| 1020 | O2 Supply Pressure Low (O2 Tank Pressure Low - No Backup) |
| | Alarm occurs when the $O_2$ supply pressure is ≤35 psig and the compressor is not able to support ventilation. If the $O_2$ source can be restored the unit should be cycled off then on to reset. By design the unit will not reestablish $O_2$ operation unless the supply pressure is ≥40 psig. If the supply pressure is between 40 and 80 psig the operator should check all hose connections for leaks. Occasionally, this alarm can be caused by a regulator that provides a static pressure within range but is not able to provide the flow necessary to meet the patient demand. |
| | Mitigation/Info: Manually Ventilate Patient, Connect 55 psig O2 then Restart, Check O2 Supply for Leaks, Replace Regulator |
| | **Replace/Service Ventilator ** |

TABLE-continued

| Service Code | Alarm Name |
|---|---|
| 1030 | Fresh Gas Intake Failure (Compressor Intake Blocked - No Backup)<br>Alarm occurs when the Fresh Gas/Emergency Air Inlet is blocked so that the compressor is not able to deliver flow sufficient for the current settings and HP $O_2$ is not available to support ventilation. The operator should clear the blockage and restart the ventilator.<br>Mitigation/Info: Manually Ventilate Patient, Clear Blocked Intake, Connect 55 psig O2, Restart Ventilator<br>\*\*Replace/Service Ventilator \*\* |
| 1041 | O2 Supply Pressure High<br>Alarm occurs when the $O_2$ supply pressure is >80 psig. Pressures above 80 psig could result in a catastrophic failure, harm to the patient and/or damage to the unit. While the patient is manually ventilated the operator or assistant should seek to reduce the $O_2$ supply pressure. Sometimes this requires changing the regulator which is not functioning as required. If the pressure cannot be reduced and a low flow device like a flow meter is available the operator can provide supplemental $O_2$ via the optional low flow $O_2$ reservoir. To clear the alarm the unit should be turned off and then restarted with supply pressure in the appropriate range (40 to 79 psig) or without HP $O_2$ connected.<br>Mitigation/Info: Manually Ventilate Patient, Decrease O2 Supply to 55 psig, Replace Regulator, Connect Low Flow O2,<br>\*\* Restart Ventilator without O2 Supply\*\* |
| 1051 | Run-Time Calibration Failure<br>Alarm occurs when there is a failure of the calibration system. When this occurs the patient should be manually ventilated, the unit removed from use and sent for service.<br>Mitigation/Info: Manually Ventilate Patient<br>\*\* Replace/Service Ventilator \*\* |
| 1052 | Airway Pressure Sensing Failure<br>Alarm occurs when communication between the airway pressure sensor and SPM is lost. When this happens the operator should manually ventilate the patient, replace the ventilator and send the unit for service.<br>Mitigation/Info: Manually Ventilate Patient<br>\*\* Replace/Service Ventilator \*\* |
| 1060 | Exhalation System Failure (Exhalation Valve Failure)<br>Alarm occurs when the exhalation control valve fails to operate. When this happens the unit stops ventilating and attempts to discharge the pressure in the breathing circuit to atmosphere. This failure may be caused by a significant blockage of the exhalation valve or an occlusion/kink in the exhalation valve tube. If possible, the operator should replace the breathing circuit and restart the ventilator. If this does not resolve the problem then the operator should manually ventilate the patient, replace the ventilator and send the unit for service.<br>Mitigation/Info: Manually Ventilate Patient, Replace Circuit and Restart<br>\*\* Replace/Service Ventilator \*\* |
| 1061 | Exhalation System Failure (Excessive Airway Pressure)<br>Alarm occurs when the airway pressure (Paw) is above 40 cm $H_2O$ or the PIP limit (when PIP limit is <35 cm $H_2O$) for >5 seconds or when the Paw is above 75 cm $H_2O$ for >1.5 seconds. When this happens the unit stops ventilating and attempts to discharge the pressure in the breathing circuit to atmosphere. This failure may be caused by a significant blockage of the exhalation valve or an occlusion/kink in the exhalation valve tube. If possible, the operator should replace the breathing circuit and restart the ventilator. If this does not resolve the problem then the operator should manually ventilate the patient, replace the ventilator and send the unit for service.<br>Mitigation/Info: Manually Ventilate Patient<br>\*\* Replace/Service Ventilator \*\* |
| 1172 | 5 Volt Self Check Failure<br>Alarm occurs when the 5 volt power bus fails to provide the required voltage. If this failure occurs, the operator should manually ventilate the patient, replace the ventilator and send the unit for service.<br>Mitigation/Info: Manually Ventilate Patient, Ventilator Not Functioning<br>\*\* Replace/Service Ventilator \*\* |
| 1173 | Internal Comm Failure (Host Device Comm Failure)<br>Alarm occurs when communication fails between one of the subcomponents the host processor. If this failure occurs, the operator should manually ventilate the patient, replace the ventilator and send the unit for service.<br>Mitigation/Info: Manually Ventilate Patient, Backup Ventilator Enabled<br>\*\* Replace/Service Ventilator \*\* |
| 1174 | Off Set Self Check Failure<br>Alarm occurs when the device is not able to calibrate the one or more transducers and is no longer able to operate safely. If this failure occurs, the operator should manually ventilate the patient, replace the ventilator and send the unit for service.<br>Mitigation/Info: Manually Ventilate Patient, Ventilator Not Functioning<br>\*\* Replace/Service Ventilator \*\* |
| 1175 | Internal Comm Failure<br>Alarm occurs when there is a failure of the internal communication bus and the host is not able to communicate with the subassemblies. If this failure occurs, the operator should manually ventilate the patient, replace the ventilator and send the unit for service.<br>Mitigation/Info: Manually Ventilate Patient, Ventilator Not Functioning<br>\*\* Replace/Service Ventilator \*\* |

TABLE-continued

| Service Code | Alarm Name |
|---|---|
| 1176 | Off Set Self Check Failure<br>Alarm occurs when the calibration file fails its integrity check. If this failure occurs, the operator should manually ventilate the patient, replace the ventilator and send the unit for service.<br>Mitigation/Info: Manually Ventilate Patient, Ventilator Not Functioning<br>** Replace/Service Ventilator ** |
| 1420 | Complete Power Failure<br>Alarm occurs when power is lost from both the internal battery and an external source during operation. When this occurs, the LCD blanks (no power for operation); the audible alarm pulses rapidly, and the visual alarm flashes rapidly. This alarm will last approximately two minutes.<br>Mitigation/Info: No LCD Display |
| 1430 | Empty Battery<br>Alarm occurs when the internal battery power drops below the amount required to provide ventilation and external power is not connected. When this occurs there is enough power to operate the user interface and provide information to the operator. The patient should be manually ventilated while an external source of power is sought. To cancel the alarm and begin operation with external power the unit must be turned off and then back on.<br>Mitigation/Info: Manually Ventilate Patient, Connect to External Power, Restart Ventilator<br>Replace/Service Ventilator |
| 1471 | Internal Comm Failure<br>Alarm occurs when the device is no longer able to communicate with the User Interface Module (UIM) and the interface controls. When this occurs ventilation continues at the current settings or the backup mode settings and the high priority alarm sounds. The patient should be manually ventilated and the ventilator sent for service.<br>Mitigation/Info: Manually Ventilate Patient, Backup Ventilator Enabled<br>** Replace/Service Ventilator** |
| 1472 | Internal Comm Failure<br>Alarm occurs when the device is no longer able to communicate with the Smart Pneumatic Module (SPM). When this occurs ventilation continues at the current settings or the backup mode settings and the high priority alarm sounds. The patient should be manually ventilated and the ventilator sent for service.<br>Mitigation/Info: Manually Ventilate Patient, Backup Ventilator Enabled<br>** Replace/Service Ventilator** |
| 1473 | Internal Comm Failure<br>Alarm occurs when no valid data is sent from the SPM within 1 second. When this occurs ventilation continues at the current settings or the backup mode settings and the high priority alarm sounds. The patient should be manually ventilated and the ventilator sent for service.<br>Mitigation/info: Manually Ventilate Patient, Backup Ventilator Enabled<br>** Replace/Service Ventilator** |
| 1474 | Internal Comm Failure<br>Alarm occurs when cyclic redundancy checking between the EMV+ and SPM fails. When this occurs ventilation continues at the current setting or the backup mode settings and the high priority alarm sounds. The patient should be manually ventilated and the ventilator sent for service.<br>Mitigation/Info: Manually Ventilate Patient, Backup Ventilator Enabled<br>** Replace/Service Ventilator** |
| 1475 | LCD Control Failure<br>Alarm occurs when the device has lost communication with the contrast control and in most instances the content of the LCD is not visible. When this occurs ventilation continues at the current settings or the backup mode setting and the high priority alarm sounds. The patient should be manually ventilated and the ventilator sent for service.<br>Mitigation/Info: Manually Ventilate Patient, Backup Ventilator Enabled<br>** Replace/Service Ventilator** |
| 1480 | SPM Compatibility Failure<br>Alarm occurs when the EMV+ and SPM software loads are not compatible. This alarm is typically associated with an SPM change where the technician failed to update the EMV+ and SPM to the current software revision. Ventilation is provided using the backup mode settings. The unit should be removed from use and sent for service.<br>Mitigation/Info: Manually Ventilate Patient, Software Compatibility Failure<br>** Replace/Service Ventilator ** |
| 1485 | Power-On Self-Check Failure<br>Alarm occurs when the Smart Pneumatic Module (SPM) software fails and is shut down. Powering the unit off allows the software to reset and may allow operation to continue.<br>Mitigation/Info: Manually Ventilate Patient, Abnormal Reset Detected, Restart Ventilator<br>** Replace/Service Ventilator ** |
| 2001 | Compressor Fault<br>Alarm occurs when the communication between the $O_2$ valve and the SPM fails and HP $O_2$ is available to provide ventilation. The alarm will continue to sound as a medium priority alarm until the user acknowledges that ventilation is being provided using HP $O_2$ by setting the FIO$_2$ to 100%. At this time the priority changes to low priority. While operating in this state the operator should assure an adequate supply of HP $O_2$. Failure to maintain the HP $O_2$ supply will result in a high priority alarm.<br>Mitigation: Operation Switched to O2 valve, Set FIO2 to 100%<br>Replace/Service Ventilator |

TABLE-continued

| Service Code | Alarm Name |
| --- | --- |
| 2002 | Compressor Fault
Alarm occurs when communication between the compressor controller and Smart Pneumatic Module (SPM) is lost and HP $O_2$ is available to provide ventilation. The alarm will continue to sound as a medium priority alarm until the user acknowledges that ventilation is being provided using HP $O_2$ by setting the $FIO_2$ to 100%. At this time the alarm priority changes to low. While operating in this state the operator should assure an adequate supply of HP $O_2$. Failure to maintain the HP $O_2$ supply will result in a high priority alarm.
Mitigation: Operation Switched to $O_2$ valve, Set FIO2 to 100%
Replace/Service Ventilator |
| 2003 | Compressor Fault (Compressor System Compressor Compromised - Backup Available)
Alarm occurs when the SPM detects a fault with the compressor flow measuring system and HP $O_2$ is available to provide ventilation. The alarm will continue to sound as a medium priority alarm until the user acknowledges that ventilation is being provided using HP $O_2$ by setting the FI02 to 100%. At this time the alarm priority changes to low. While operating in this state the operator should assure an adequate supply of HP $O_2$. Failure to maintain the HP $O_2$ supply will result in a high priority alarm.
Mitigation: Flow Measurement Problem Detected, Operation Switched to $O_2$ Valve, Ventilate at $FIO_2$ = 100%.
Replace/Service Ventilator |
| 2011 | O2 Valve Fault
Alarm occurs when the signal to the $O_2$ valve is outside of the calibration range for the required flow rate and the compressor is available to provide ventilation. The medium priority alarm will continue until the user acknowledges that ventilation is being provided using the compressor by setting the $FIO_2$ to 21%. At this time the alarm priority changes to low priority. While operating in this state the operator should monitor the $SpO_2$ to assure that adequate oxygenation is maintained. If low flow $O_2$ is available it can be entrained through the Fresh Gas/Emergency Air Intake port using the optional $O_2$ reservoir. Maintain an acceptable $SpO_2$ by adjusting the $O_2$ supply up or down to increase or decrease the amount of $O_2$ delivered to the patient.
Mitigation: Operation Switched to Compressor, Set FIO2 To 21%, Connect Low Flow O2, Monitor SpO2
Replace/Service Ventilator |
| 2012 | O2 Valve Fault
Alarm occurs when the communication between the $O_2$ valve and the SPM fails and the compressor is available to provide ventilation. The alarm will continue to sound as a medium priority alarm until the user acknowledges that ventilation is being provided using the compressor by setting the $FIO_2$ to 21%. At this time the alarm priority changes to low. While operating in this state the operator should monitor the $SpO_2$ to assure that adequate oxygenation is maintained. If low flow $O_2$ is available it can be entrained through the Fresh Gas/Emergency Air Intake port using the optional $O_2$ reservoir. Maintain an acceptable $SpO_2$ by adjusting the $O_2$ supply up or down to increase or decrease the amount of $O_2$ delivered to the patient.
Mitigation/Info: Operation Switched to Compressor, Set FIO2 To 21%, Connect Low Flow $O_2$, Monitor SpO2
Replace/Service Ventilator |
| 2020 | O2 Supply Pressure Low
Alarm occurs when the $O_2$ supply pressure is <35 psig and the compressor is able to support ventilation. When this occurs the unit begins ventilation using the compressor. The alarm will continue to sound as a medium priority alarm until the user acknowledges that ventilation is being provided using the compressor by setting the $FIO_2$ to 21%. Pressing the MUTE/CANCEL button cancels this alarm completely.
NOTE: The device is designed to work with or without external $O_2$. If HP $O_2$ is connected the unit will not continue $O_2$ operation unless the supply pressure is ≥40 psig. This is done to prevent continuous cycling between alarms during the inspiratory phase and no alarm during the expiratory phases. If low flow $O_2$ is available it can be entrained through the Fresh Gas/Emergency Air Intake port using the optional $O_2$ reservoir. Maintain an acceptable $SpO_2$ by adjusting the $O_2$ supply up or down to increase or decrease the amount of $O_2$ delivered to the patient.
Mitigation/Info: Operation Switched to Compressor, Check O2 Supply Pressure, Check/Replace Regulator, Set FIO2 to 21%. Connect Low Flow O2, Monitor SpO2
Replace/Service Ventilator  |
| 2030 | Fresh Gas Intake Fault
Alarm occurs when the Fresh Gas/Emergency Air Inlet is blocked so that the compressor is not able to deliver a breath within ±10% of the current settings and HP $O_2$ is available to support ventilation. When this occurs the ventilator immediately switches to HP $O_2$ powered ventilation. To clear the alarm first set the $FIO_2$ to 100% to acknowledge that the patient is being ventilated at 100%, clear the blockage and then set the $FIO_2$ back to the original value. If the blockage has been cleared operation with the compressor will restart. If the blockage cannot be cleared, the alarm will resound, continue ventilation with $FIO_2$ set to 100% and assure an adequate supply of HP $O_2$.
Mitigation/Info: Operation Switched to O2 Valve, Clear Blocked Intake, Set FIO2 to 100%, Monitor SpO2
Replace/Service Ventilator  |

TABLE-continued

| Service Code | Alarm Name |
|---|---|
| 2053 | Suspicious Triggers<br>Alarm occurs when airway pressure sensor fails to calibrate during the expiratory phase of a breath. When this occurs the unit attempts to reestablish a baseline by momentarily setting PEEP to 0 cm H$_2$0 and suspending triggered breaths. This interruption lasts no longer than 2 breath cycles. The operator should also check for leaks in the hose and tubes; patient airway and exhalation valve. If recalibration is successful the alarm will automatically cancel. If it cannot, the patient should be manually ventilated; the unit should be replaced and sent for service.<br>Mitigation/Info: Attempting Self Calibration, Momentarily Disabling Triggers and PEEP, Check Circuit For Leaks/Disconnects, Check Tube Placement/Cuff<br>Replace/Service Ventilator |
| 2062 | Exhalation Fault<br>Alarm occurs when the airway pressure (Paw) measured at the end of expiration is >5 cm H20 above the baseline pressure (PEEP pressure). This is typically caused by a restriction of the exhalation valve or an occlusion/kink in one or more of the breathing circuit tubes or hose. If the breathing circuit tubes appear to be intact the circuit should be replaced to eliminate the possibility of a bad exhalation valve. If the condition does not resolve the operator should manually ventilate the patient, replace the ventilator.<br>Mitigation/Info: Check Circuit for Kinked Hose/Tube, Check for Blocked Exhalation Valve, Replace Circuit, Replace/Service Ventilator<br>** Manually Ventilate Patient** |
| 2070 | Airway Pressure High<br>Alarm occurs when the Paw is greater than the high airway pressure limit. When this occurs flow decelerates to maintain Paw at the high airway pressure limit for the duration of the breath (inspiratory time). The operator should check for kinks or blockage of the breathing circuit, exhalation valve or patient airway. In some instances the cause can be an accumulation of secretions in the airway which will require suctioning to clear. The operator should also assess if the patient is fighting the ventilator (dyssynchrony) or if the high airway pressure limit is set too low.<br>Mitigation/Info: Pressure Exceeds Limit Setting, Check Circuit for Kinked Hose/Tube, Check for Airway Obstruction, Suction Airway if Necessary, PIP Limit Set Too Low?<br>** Manually Ventilate Patient** |
| 2071 | Low Airway Pressure<br>Alarm occurs when the Paw is less than the low airway pressure limit. When this occurs flow increases to maintain the Paw for the duration of the breath (inspiratory time). The operator should check for leaks/disconnects in the breathing circuit, patient airway or a failure of the exhalation valve. The operator should also assess if the patient is breathing with the ventilator (dissynchrony) or if the low airway pressure limit is set too high. If a replacement is available the operator should replace the breathing circuit. If these mitigations do not resolve the alarm condition then, the ventilator should be replaced and sent for service.<br>Mitigation/Info: Check Patient Connection, Check Circuit For Loose Hose/Tube, Check Exhalation Valve, Check Tube Placement/Cuff, Is Low Limit Set Correctly?<br>** Manually Ventilate Patient** |
| 2072 | High Tidal Volume<br>Alarm occurs when operating with a pressure target and the delivered tidal volume exceeds the operator defined limit. This can be caused by a leak in the patient connection or breathing circuit. When the ventilator is not able to reach the pressure target flow increases to compensate which leads to the high delivered tidal volume. The operator should check for leaks/disconnects in the breathing circuit, patient airway or a failure of the exhalation valve. The operator should also assess if the patient is anxious and breathing deeply or if the high tidal volume limit is set too low. If a replacement is available the operator should replace the breathing circuit.<br>Mitigation/Info: Check Patient Connection, Check Circuit For Loose Hose/Tube, Check Exhalation Valve, Check Tube Placement/Cuff, Is High Limit Set Correctly?<br>** Monitor Patient** |
| 2073 | Low Tidal Volume<br>Alarm occurs when operating with a pressure target and the delivered tidal volume does not reach the operator defined limit. When this occurs flow decelerates to maintain the Paw at airway pressure limit for the duration of the breath (inspiratory time). If the PIP setting is set properly the breath should be greater than the low limit (provided it is set properly as well). The operator should check for kinks or blockage of the breathing circuit or patient airway. In some instances the cause can be an accumulation of secretions in the airway which will require suctioning to clear. The operator should also assess if the patient is fighting the ventilator (dissynchrony) or if the high airway pressure limit is set too low.<br>Mitigation/Info: Check Circuit For Kinked Hose/Tube, Check For Airway Obstruction, Suction Airway If Necessary, Volume Limit Too Low?<br>** Manually Ventilate Patient** |

TABLE-continued

| Service Code | Alarm Name |
|---|---|
| 2074 | High Breath Rate<br>Alarm occurs when the actual breathing rate (set rate plus spontaneous patient rate) exceeds the high alarm limit. This can be caused by the patient breathing too fast due to anxiety or pending respiratory failure. It can also be caused by autotriggering due to a leak or the when the spontaneous/assisted breath trigger is set too close to the baseline pressure (PEEP). The operator should check for leaks/disconnects in the breathing circuit, patient airway or a failure of the exhalation valve. The operator should also assess if the patient is anxious and breathing deeply or if the high tidal volume limit is set too low. If a replacement is available the operator should replace the breathing circuit.<br>Mitigation/Info: Check For Loose Hose/Tube, Is Trigger Level Too Sensitive, Is High Alarm Limit Set Correctly?<br>** Consult Physician ** |
| 2075 | Low Breath Rate/Apnea<br>Alarm occurs when the actual breathing rate (set rate plus spontaneous patient rate) is less than the low alarm limit. This can be caused by the patient not breathing or breathing at a rate less than the limit. If the spontaneous/assisted breath trigger is not sensitive enough the patient may not be able to trigger breaths. The operator should also determine if the low rate is set too high for the patient.<br>Mitigation/Info: Is Patient Breathing Spontaneously?, Is Trigger Level Sensitive Enough?, Is Low Alarm Limit Set Correctly?, Increase Ventilation Support<br>** Manually Ventilate Patient** |
| 2090 | PEEP Leak<br>Alarm occurs when Paw drops below the PEEP setting by 2 cm $H_2O$ during the expiratory phase of the breath. This can be caused by a leak in the breathing circuit, exhalation valve or patient airway. The operator should check the breathing circuit and exhalation valve to assure that all connections are tight. When the circuit appears damaged or is suspect it should be replaced. The operator should also check if there is a leak around the cuff of the patient's airway. If these mitigations do not resolve the alarm condition then, the ventilator should be replaced and sent for service.<br>Mitigation/Info: Check Patient Connection, Check Circuit For Loose Hose/Tube, Check Exhalation Valve, Check Tube Placement/Cuff<br>** Replace Circuit** |
| 2091 | Gas Trapped<br>Alarm occurs when the exhaled flow from the patient continues throughout the expiratory period causing the expiratory control valve to cycle throughout the period to maintain the baseline pressure. When this occurs the operator should increase the expiratory period by decreasing the inspiratory time, decreasing the breathing rate or both. The physician should also be consulted.<br>Mitigation/Info: Incomplete Exhalation, Increase Expiratory Time, Decrease Inspiratory Time, Decrease Respiratory Rate<br>** Consult Physician** |
| 2095 | Insufficient Flow<br>Alarm occurs when the pressure target is not reached during the inspiratory period during pressure targeted ventilation. Typically this can occur when the ventilator is configured to start with pediatric settings and the max flow has been set below 100 liters/min in anticipation of the pediatric patient. The default setting for adult breathing is 100 liters/min. To adjust the max flow, press and hold the BPM parameter button (during pressure targeted breathing) and adjust the max flow up or down based on the patient flow requirement. If the flow cannot be adjusted appropriately then the patient should be ventilated using volume targeted ventilation.<br>Mitigation/Info: Pressure Target Not Met, Increase Max Flow, Press/Hold BPM Button<br>** Ventilate With Volume Target** |
| 2100 | Patient Disconnect<br>Alarm occurs when the Paw fails to exceed the PEEP setting by ~7 cm $H_2O$. When this occurs the operator should quickly check the patient connection, breathing circuit connections and the exhalation valve. At times this alarm can be caused by the patient breathing with the ventilator during inspiration which prevents the Paw from passing the minimum pressure. While resolving the alarm condition the operator should be sure to manually ventilate the patient.<br>Mitigation/Info: Check Patient Connection, Check Circuit for Loose Hose/Tube, Check Exhalation Valve, Patient Breathing With Ventilator?, Replace Circuit<br>Manually Ventilate Patient |
| 2300 | Pulse Ox Module Failed<br>Alarm occurs when the pulse oximeter module fails while in use. There is no operator intervention. When the alarm is active "-- --" will display in the HR and SpO2 windows. Pressing the Mute/Cancel button silences the audible alarm for 30 seconds. To resolve the alarm, remove the probe from the unit and turn off the pulse oximeter function, in the user menu.<br>Mitigation/Info: Internal Failure, SpO2/HR Not Available, Turn Off Pulse Ox<br>Replace/Service Ventilator |
| 2301 | Internal Comm Failed<br>Alarm occurs when the communication between the pulse oximeter module and unit fails. When this occurs the operator is required to turn off the pulse oximeter monitor to end the alarm condition. When this is done "off" appears in the data windows for $SpO_2$ and HR as those parameters are no longer available. When appropriate the operator should replace the ventilator and send it for service.<br>Mitigation/Info: Pulse Ox Module Failure, SpO2/HR Not Available, Turn Off Pulse Ox<br>Replace/Service Ventilator |

TABLE-continued

| Service Code | Alarm Name |
|---|---|
| 2314 | SpO2 Sensor Off Patient<br>Alarm occurs when an operating sensor losses the patient signal. The most common cause is when the sensor disconnects from the patient or is misaligned with the sensor site. This alarm can also be caused by poor perfusion at the sensor site which doesn't allow for a reading. In these cases try another site. Replace the sensor if another sensor is available. If the alarm condition cannot be resolved the operator should turn off pulse oximetry monitoring.<br>Mitigation/Info; Check $SpO_2$ Sensor Site, Check Patient for Peripheral Pulse, Change Site, Check Sensor Operation, Replace Sensor<br>\*\*Turn Off $SpO_2$ Monitoring. \*\* |
| 2401 | SpO2 Low<br>Alarm occurs whenever the $SpO_2$ value drops below the Low $SpO_2$ Limit. The default value for the limit is 94%. Corrective actions are increasing oxygenation by increasing the $FIO_2$ or PEEP settings. PEEP should only be changed based on consultation with the attending physician. When using low-flow $O_2$ the operator should increase the flow of $O_2$ into the optional low flow $O_2$ reservoir.<br>Mitigation/Info: $SpO_2$ Below Limit, Increase $FIO_2$, Check $O_2$ Supply, Increase PEEP Per Physician Order<br>\*\*Consult Physician\*\* |
| 2410 | Heart Rate High<br>Alarm occurs when the heart rate is greater than the High Heart Rate Limit. The default value for the limit is 120 beats/minute. The operator should consult with the attending physician on how best to reduce the heart rate to an acceptable level.<br>Mitigation/Info: Heart Rate Above Limit<br>\*\*Consult Physician\*\* |
| 2411 | Heart Rate Low (Pulse Rate Low)<br>Alarm occurs when the heart rate is less than the Low Heart Rate Limit. The default value for the limit is 40 beats/minute. The operator should consult with the attending physician on how best to increase the heart rate to an acceptable level.<br>Mitigation/Info: Heart Rate Below Limit<br>\*\*Consult Physician\*\* |
| 2421 | Input Protection Circuit Failed<br>Alarm occurs when there is a failure of the input protection circuit and the unit is able to operate. The alarm will continue until the unit is turned off. The operator can mute the alarm for 30 seconds by pushing the MUTE/CANCEL button. The operator should replace the unit and send it for service.<br>Mitigation/Info: Input protection circuit failure, Power System Needs Repair<br>\*\*Replace/Service Ventilator\*\* |
| 2423 | Power Circuit Hardware Fault<br>Alarm occurs when the internal power circuit has failed and external power is connected but cannot be used. The fault cannot be repaired by the operator. Pressing the Mute/Cancel button silences the audible alarm for 30 seconds.<br>Mitigation/Info: Power System Needs Repair, Internal Battery Operation<br>\*\* Replace/Service Ventilator\*\* |
| 2430 | Low Battery<br>Alarm occurs when the unit detects that there is ≤5 minutes of battery operation remaining and external power is not connected. The operator should immediately seek a source of external power and/or plan to provide manual ventilation. Attaching external power will immediately clear the alarm though a low priority alarm will be maintained until the internal battery has recharged so that the unit can provide 30 minutes of operating time (~5 to 10 minutes).<br>Mitigation/Info: Less Than 5 Minutes Operation, Connect External Power, Assure Ability to Manually Ventilate<br>\*\* Replace/Service Ventilator\*\* |
| 2450 | Battery Fault - No External Power Connected<br>Alarm occurs when the battery temperature reaches 70° C. (158° F.) which is 5° C. from its maximum operating temperature using the internal battery and external power is not connected. When the battery temperature reaches 75° C. (167° F.) the battery will shut down to prevent failure and the unit will sound a high priority alarm and shutdown. If possible the operator should provide a source of external power which would allow operation to continue at the current and higher temperatures. In addition, the unit should be removed from the soft case which acts as insulation. Shading the patient and ventilator from direct sunlight may also help reduce the battery temperature.<br>Mitigation/Info: Battery Within 5° C. of High Limit, Remove Padded Case, Connect External Power, Assure Ability to Manually Ventilate, Shade Patient and Ventilator<br>\*\*Move To Cooler Location\*\* |
| 2455 | Battery Fault - No External Power Connected<br>Alarm occurs when the EMV+ is not able to communicate with the internal battery. When this occurs the device does not know the current charge in the batter and operation could stop at anytime. To continue operation and the operator should connect external power and assure the ability to manually ventilate the patient. When external power is connected the alarm priority decreases to Low Priority.<br>Mitigation/Info: Battery Comm Failure, Connect External Power, Assure Ability to Manually Ventilate Patient<br>\*\*Replace/Service Ventilator\*\* |

TABLE-continued

| Service Code | Alarm Name |
|---|---|
| 3001 | Compressor Fault<br>Alarm occurs when the compressor fails to operate or fails to provide the flow required to deliver a breath within ±10% of the current settings, HP $O_2$ is available to provide ventilation and the operator has set the $FIO_2$ to 100%. While operating in this state the operator should assure an adequate supply of HP $O_2$. Failure to maintain the HP $O_2$ supply will result in a high priority alarm.<br>Mitigation: Assure 55 psig O2, O2 Operation Only!<br>\*\*Replace/Service Ventilator\*\* |
| 3002 | Compressor Fault<br>Alarm occurs when communication between the compressor controller and SPM is lost, HP $O_2$ is available to provide ventilation and the operator has set the $FIO_2$ to 100%. While operating in this state the operator should assure an adequate supply of HP $O_2$. Failure to maintain the HP $O_2$ supply will result in a high priority alarm.<br>Mitigation: Assure 55 psig O2 Supply, O2 Operation Only!<br>\*\*Replace/Service Ventilator\*\* |
| 3011 | O2 Valve Fault<br>Alarm occurs when the signal to the $O_2$ valve is outside of the calibration range for the required flow rate, the compressor is available to provide ventilation and the operator has acknowledged that ventilation is being provided using the compressor by setting the $FiO_2$ to 21%. While operating in this state the operator should monitor the $SpO_2$ to assure that adequate oxygenation is maintained. If low flow $O_2$ is available it can be entrained through the Fresh Gas/Emergency Air Inlet port using the optional $O_2$ reservoir. Maintain an acceptable $SpO_2$ by adjusting the $O_2$ supply up or down to increase or decrease the amount of $O_2$ delivered to the patient.<br>Mitigation: Compressor Operation Only!, Keep FIO2 at 21%, Connect Low Flow O2, Monitor SpO2<br>\*\*Replace/Service Ventilator\*\* |
| 3012 | O2 Valve Fault<br>Alarm occurs when communication between the $O_2$ valve is lost, the compressor is available to provide ventilation and the operator has set the $FIO_2$ to 21%. While operating in this state the operator should monitor the $SpO_2$ to assure that adequate oxygenation is maintained. If low flow $O_2$ is available it can be entrained through the Fresh Gas/Emergency Air Inlet port using the optional $O_2$ reservoir. Maintain an acceptable $SpO_2$ by adjusting the $O_2$ supply up or down to increase or decrease the amount of $O_2$ delivered to the patient.<br>Mitigation/Info: Operation Switched to Compressor!, Keep FIO2 at 21%, Connect Low Flow O2, Monitor SpO2<br>\*\*Replace/Service Ventilator\*\* |
| 3030 | Fresh Gas Intake Fault<br>Alarm occurs when the Fresh Gas/Emergency Air Inlet is blocked so that the compressor is not able to deliver breaths within ±10% of the current settings, HP 02 is available to support ventilation and the operator has set the $FIO_2$ to 100%. To clear the alarm, clear the blockage and set the $FIO_2$ back to the original value. If the blockage is cleared operation with the compressor will restart. If the blockage is not cleared, the alarm will resound, set the $FIO_2$ to 100%, continue ventilation and assure an adequate supply of HP $O_2$.<br>Mitigation/Info: O2 Valve Operation, Clear Blocked Intake & Retry Compressor, Keep FIO2 at 100%, Monitor SpO2<br>\*\*Replace/Service Ventilator \*\* |
| 3031 | Fresh Gas Intake Fault<br>Alarm occurs when the Fresh Gas/Emergency Air Inlet is blocked but is still capable of delivering breaths within ±10% of the current settings. This could be caused by an external blockage or a dirty external or internal filter (refer to instructions for changing the internal filter). If the blockage is cleared the alarm will automatically cancel.<br>Mitigation/Info: Clear Restricted Intake<br>\*\*Replace/Service Ventilator \*\* |
| 3032 | Fresh Gas Intake Fault<br>Alarm occurs when communication between the Fresh Gas/Emergency Air Inlet pressure sensor has been lost. Normal operation can continue but, if the condition is not cleared by powering off and restarting the unit should be sent for service. When used during this alarm condition the operator should be sure to keep the Fresh Gas/Emergency Air Inlet clear and assure that external filters are checked regularly.<br>Mitigation/Info: Intake Pressure Sensor Failure, Unable to Detect Filter Obstruction<br>\*\*Replace/Service Ventilator \*\* |
| 3041 | O2 Supply Pressure High<br>Alarm occurs when the $O_2$ supply pressure is ≥75 psig. The alarm automatically cancels when the supply pressure drops below 66 psig. Pressures above 80 psig could result in a catastrophic failure, harm to the patient and/or damage to the unit. The operator should seek to reduce the O2 supply pressure, sometimes this requires replacing the regulator which is not functioning as required. If the pressure cannot be reduced and a low flow device like a flow meter is available the operator can provide supplemental $O_2$ via the optional low flow $O_2$ reservoir. If not, the operator should monitor the HP $O_2$ supply pressure and assure that the pressure does not rise further.<br>Mitigation/Info: Decrease $O_2$ Supply Pressure, Replace Regulator, Connect Low Flow $O_2$, Monitor $SpO_2$<br>\*\* Restart Ventilator without HP $O_2$ \*\* |

TABLE-continued

| Service Code | Alarm Name |
|---|---|
| 3110 | RTC Battery Fault<br>Alarm occurs when the real-time clock (RTC) battery is <~2.5 volts. The alarm condition is checked at start up and if this alarm occurs the unit is safe to operate but the operator should look to take the unit out of service when appropriate and send it for service. Changing the battery requires opening the unit and should only be done by a trained service technician. The RTC battery provides power for the storage of critical information used by the ventilator during startup.<br>Mitigation/Info: RTC Battery Low, Schedule Service Immediately<br>\*\*Replace/Service Ventilator\*\* |
| 3120 | Self Check Fault<br>Alarm occurs at start up when the preselected number of days has elapsed from the last calibration. When appropriate the unit should be sent for service. The low priority message serves as a reminder. Calibration is due every 365 days. Operators should schedule the unit for service as soon as possible.<br>Mitigation/Info: Calibration Due, Schedule Service Immediately<br>\*\*Replace/Service Ventilator\*\* |
| 3130 | Ambient Pressure Fault (Excessive Altitude Sensor Failure)<br>Alarm occurs when the ambient pressure transducer fails. When this occurs, the unit is no longer able to automatically compensate for changes in altitude especially in situations where the ambient pressure could change rapidly as during air transport. When used in these conditions the operator should monitor the airway pressure and reduce the tidal volume to maintain the airway pressure as altitude is increased. During descent, the tidal volume should be increased to maintain Paw if it was adjusted while at altitude. Operators should also monitor chest rise and breath sounds to assure adequate ventilation.<br>Mitigation/Info: Barometric Pressure Sensor, Altitude Compensation Disabled, Maintain Airway Pressure, Check Patient Chest Rise, Avoid Use At Varying Altitude<br>\*\*Replace/Service Ventilator\*\* |
| 3131 | Ambient Pressure Fault (Excessive Altitude)<br>Alarm occurs when the ambient pressure transducer detects an altitude >25,000 feet (7620 meters). Beyond this altitude compensation remains fixed at the 25,000 ft compensation level. The operator should monitor the Paw and reduce the tidal volume as altitude increases. During descent the tidal volume should be increased to its original value once the unit has returned to the compensated altitude. Where possible cabin pressure should be maintained in the compensated range.<br>Mitigation/Info: Excessive Altitude Detected, Beyond Altitude Compensation Limit, Maintain Airway Pressure, Check Patient Chest Rise, Monitor Ventilator/Patient<br>\*\*Reduce Altitude\*\* |
| 3132 | Ambient Pressure Fault (Excessive Altitude)<br>Alarm occurs when the ambient pressure transducer detects an altitude <-2,000 feet below sea level (610 meters, 15.8 psig or 1089 mb). This state can be caused by use in subterranean rescue operation or mistaken use in a hyperbaric chamber. Beyond this pressure level compensation remains fixed at the −2,000 ft level.<br>NOTE: the EMV+ is not intended for use in hyperbaric chambers or at hyperbaric pressures.<br>Mitigation/Info: High Barometric Pressure Detected, Beyond Compensation Limit, Maintain Airway Pressure, Check Patient Chest Rise, Monitor Ventilator/Patient<br>\*\*Reduce Ambient Pressure\*\* |
| 3140 | Operational Temperature Fault (Excessive Temperature High)<br>Alarm occurs when the ambient temperature exceeds the normal operating range (>131° F., 55° C.) for the ventilator. The unit allows operation at these temperatures but alerts the operator to the condition. Operating above the specified range can affect the longevity of the internal battery and the duration of operating time. When operating at high temperatures the operator should remove the softcase which insulates and increases the ventilator's internal temperature.<br>Mitigation/Info: High Temperature Detected, Remove Padded Case,<br>\*\*Monitor Ventilator\*\* |
| 3141 | Operational Temperature Fault (Excessive Temperature Low)<br>Alarm occurs when the ambient temperature falls below the normal operating range (<14° F., −10° C.) for the ventilator. The unit allows operation at these temperatures but alerts the operator to the condition. Operating below the specified range can affect the longevity of the internal battery and the duration of operating time. At extreme cold temperatures operating time can be significantly reduced. When operating at low temperatures the operator should use the softcase which insulates and increases the ventilator's internal temperature.<br>Mitigation/Info: Low Temperature Detected, Use Padded Case<br>\*\*Monitor Ventilator\*\* |
| 3143 | Self Check Fault<br>Alarm occurs when the failure of the internal temperature sensors. When this occurs the unit is not longer able to detect if it is operating outside of the allowable temperature range. If operating inside of the standard temperature range −25° C. to 49° C. (−13° F. to 120° F.) there is not affect on operation. If operating outside this range the operator should monitor the unit continuously. When appropriate the operator should replace the ventilator and send it for service.<br>Mitigation/Info: Temperature Sensor Fault, Temperature Changes Do Not Affect Autocal Cycle, Schedule Service Immediately<br>\*\*Replace/Service Ventilator\*\* |

TABLE-continued

| Service Code | Alarm Name |
|---|---|
| 3300 | SpO2 Shutdown (MS 11 Failure - Monitor Not In Use)<br>Alarm occurs when the pulse oximeter module fails and the operator has turned off pulse oximeter monitoring acknowledging the condition. When this is done "off" appears in the data windows for $SpO_2$ and HR as those parameters are no longer available. When appropriate the operator should replace the ventilator and send it for service.<br>Mitigation/Info: Internal Failure, SpO2/HR Not Available<br>Replace/Service Ventilator |
| 3301 | SpO2 Shutdown (Comm Failure EMV-Pulse Ox - Monitor Not In Use)<br>Alarm occurs when the communication between the pulse oximeter module and unit fails and the operator has turned off pulse oximeter monitoring acknowledging the condition. When this is done "-- --" appears in the data windows for $SpO_2$ and HR as those parameters are no longer available. When appropriate the operator should replace the ventilator and send it for service.<br>Mitigation/Info: Pulse Oximeter Module Failure<br>Replace/Service Ventilator |
| 3310 | No SpO2 Sensor Connected (No Sensor Connected)<br>Alarm occurs when the pulse oximeter detects that no $SpO_2$ sensor is connected after a period of successful operation.<br>NOTE: during start up the unit automatically detects if a sensor is connected. If it is, the unit begins operation with the pulse oximeter active. If no sensor is detected the unit turns off this function.<br>If the sensor is properly connected this failure can also be the result of a broken or defective sensor. If the alarm condition cannot be resolved the operator should remove the sensor and turn off pulse oximetry monitoring in the user menu.<br>Mitigation/Info: Check Pulse Ox Sensor, Check Sensor/Ventilator Connection, Reinsert Sensor, Cable/Sensor Damaged?, Replace Sensor<br>Turn Off Pulse Ox Monitoring |
| 3311 | Defective Sensor<br>Alarm occurs when the pulse oximeter cannot identify the connected sensor or the sensor has failed. Causes for this alarm include broken sensor cable, inoperative LEDs and/or faulty detector. If the alarm condition cannot be resolved the operator should turn off pulse oximetry monitoring.<br>Mitigation/Info: Check $SpO_2$ Sensor, Check Sensor Connector at Ventilator, Reinsert Sensor, Cable/Sensor Damaged?, Replace Sensor<br>Turn Off $SpO_2$ Monitoring |
| 3312 | SpO2 Pulse Search<br>Alarm occurs when the pulse oximeter is searching for a pulse. If values are not displayed within 30 seconds disconnect and reconnect sensor and reapply to patient. If pulse search continues, remove sensor and replace on a better perfused site. Replace the sensor if another sensor is available. If the alarm condition cannot be resolved the operator should turn off pulse oximetry monitoring.<br>Mitigation/Info: Please Wait, Check Sensor Placement/Change Site, Minimize Patient Movement, Check Sensor Operation/Replace<br>Turn Off $SpO_2$ Monitoring |
| 3313 | SpO2 Signal Interference<br>Alarm occurs when an outside signal or energy source prevent accurate reading by the device. When this occurs the patient should be moved from the location or pulse oximeter turned off.<br>Mitigation/Info: External Signal Interfering With Measurement, Remove Patient From Location<br>Turn Off $SpO_2$ Monitoring |
| 3315 | Too Much Ambient Light<br>Alarm occurs when there is too much ambient light on the $SpO_2$ sensor or there is inadequate tissue covering the sensor detector. Most often this alarm condition can be resolved by shielding the sensor from ambient light.<br>Mitigation/Info: Shield Sensor From Light, Change Sensor Location, Check Sensor Operation, Replace Sensor<br>Turn Off $SpO_2$ Monitoring |
| 3316 | Invalid SpO2 Sensor (Unrecognized Sensor)<br>Alarm occurs does when the pulse oximeter does not recognize the connected sensor. The alarm can also occur when there is a broken sensor cable, inoperative LEDs, a fault is detected and/or the sensor has failed. To resolve the alarm condition the sensor should be replaced. If the alarm condition cannot be resolved the operator should turn off pulse oximetry monitoring.<br>Mitigation/Info: Replace Sensor<br>Turn Off $SpO_2$ Monitoring |
| 3317 | Low SpO2 Perfusion (Low Perfusion)<br>Alarm occurs whenever the amplitude of the arterial pulsation is weak. Low perfusion typically occurs in patients with poor circulation or when the sensor is applied to the same limb as the noninvasive blood pressure (NIBP) cuff. To resolve the alarm condition, move the sensor to a better perfused site or to another limb if the interference is from the NIBP cuff.<br>Mitigation/Info: Arterial Pulsation Weak, Check Sensor Site, Change Sensor Site, Check Sensor Operation<br>Turn Off $SpO_2$ Monitoring |

TABLE-continued

| Service Code | Alarm Name |
|---|---|
| 3318 | Low SpO2 Perfusion (poor SpO2 signal)<br>Alarm occurs when the pulse oximeter determines the quality of the input signal is low due to excessive motion or artifact. To resolve the alarm minimize patient movement and make sure the sensor is properly applied.<br>Mitigation/Info: Signal Artifact, Minimize Patient Movement, Check Sensor Placement, Check Sensor Operation<br>\*\*Turn Off $SpO_2$ Monitoring\*\* |
| 3421 | External Power Fail/Disconnect<br>Alarm occurs when the external power (either AC or DC) drops below minimum level (5 VDC as supplied by either the AC/DC Power Supply or a direct DC source) or power is intentionally disconnected. Since the unit is designed to operate with either external power or using its internal battery this is a low priority alarm that clears when the operator presses the MUTE/CANCEL button. Pressing the MUTE/CANCEL button is the operator's acknowledgement that the unit is operating on internal battery. If this alarm occurs and the operator believes that the unit is still connected to external power the operator should investigate the external power source.<br>Mitigation/Info: Internal Battery Operation, Check Power Connection/Supply, Monitor Battery Status<br>\*\*Replace/Service Ventilator\*\* |
| 3422 | Missing Battery<br>Alarm occurs when the internal battery has been removed or communication between the battery and CPU has failed. When external power is applied the unit is capable of operation however, loss of external power will result in loss of ventilation and a high priority alarm. Operating in this state should only be done when no other alternatives are available.<br>Mitigation/Info: No Battery Detected, DO NOT Remove External Power!, Maintain External Power<br>\*\*Replace/Service Ventilator\*\* |
| 3430 | Low Battery (Low Battery - Warning)<br>Alarm occurs when the unit detects that there are ≤30 minutes of battery operation remaining and no external power is connected. The operator should seek a source of external power and/or plan to provide manual ventilation. Attaching external power will immediately clear the alarm to a low priority alarm and will be maintained until the internal battery has recharged so that the unit can provide at least 30 minutes of operating time.<br>Mitigation/Info: Less Than 30 Minutes Operation, Connect External Power, Assure Ability to Manually Ventilate<br>\*\* Replace/Service Ventilator\*\* |
| 3431 | Low Battery<br>Alarm occurs when operating with external power and the unit detects that there are ≤30 minutes of internal battery backup available. The unit is warning the operator that in the event of an external battery failure the unit ≤30 minutes of backup.<br>NOTE: The unit does not charge the internal battery when attached to an external battery.To resolve the alarm condition the operator must attach the unit to a continuous external AC or DC source to recharge the internal battery. If this is not possible operation can continue as long as power is supplied by the external battery.<br>Mitigation/Info: Less Than 30 Minutes Internal Backup, Operating With External Power, Continue Charging With External Power, Assure Ability To Manually Ventilate<br>\*\*Replace/Service Ventilator\*\* |
| 3441 | External Power Failed (External Power High)<br>Alarm occurs when the supplied DC power is >33 VDC. When this occurs the unit automatically switches to operation using the internal battery. If the supplied power drops to <30 VDC the unit automatically returns to operation using external power. If the external power source is known to be good then the AC/DC Power Supply may be faulty and need replacement.<br>Mitigation/Info: External Voltage Too High, Internal Battery Operation, Check/Replace Power Supply, Change Power Source<br>\*\*Replace/Service Ventilator\*\* |
| 3444 | External Power Failed<br>Alarm occurs when the voltage polarity is reversed when the unit is attached to an external DC source. When this occurs the unit automatically switches to operation using the internal battery. This condition is most likely caused by a faulty DC source. The operator should seek an alternate power source.<br>Mitigation/Info: DC Voltage Reversed, Internal Battery Operation, Disconnect Power Source<br>\*\*Replace Power Source\*\* |
| 3450 | Battery Fault (Battery Nearly Too Hot for Discharge - w/External Power Connected)<br>Alarm occurs when the battery temperature reaches 70° C. (158° F.) which is 5° C. from its maximum operating temperature and external power is connected. When the battery temperature reaches 75° C. (167° F.) the battery will shut down to prevent failure. When this occurs the unit will continue operation using external power only. The unit should be removed from the soft case which acts as insulation. Shading the patient and ventilator from direct sunlight may also help reduce the battery temperature.<br>Mitigation/Info: Battery Within 5° C. of High Limit, Remove Padded Case, Continue External Power Operation, Shade Patient and Ventilator<br>\*\*Move To Cooler Location\*\* |
| 3451 | Battery Fault (Battery Too Hot for Discharge w/External Power Connected)<br>Alarm occurs when the battery temperature reaches ≥75° C. (167° F.) and external power is connected. Discharging the battery beyond this temperature could destroy the battery and damage the unit. During the alarm condition the unit will continue operation using external power. The unit should be removed from the soft case which acts as insulation. Shading the |

TABLE-continued

| Service Code | Alarm Name |
|---|---|
| | patient and ventilator from direct sunlight may also help reduce the battery temperature.<br>Mitigation/Info: Battery Too Hot to Discharge, Do Not Remove External Power!, Remove Padded Case, Assure Ability to Manually Ventilate Patient, Shade Patient and Ventilator<br>\*\*Move To Cooler Location\*\* |
| 3452 | Battery Fault (Battery Too Hot for Charging)<br>Alarm occurs when the battery temperature is >45° C. (122° F.). Charging the battery above this temperature could destroy the battery and damage the unit. During the alarm condition the unit continues to operate using external power and if external power is lost the unit will operate using internal battery power. The unit should be removed from the soft case which acts as insulation. Shading the patient and ventilator from direct sunlight may also help reduce the battery temperature.<br>Mitigation/Info: Battery Too Hot To Charge, Remove Padded Case, Shade Patient and Ventilator<br>\*\*Move To Cooler Location\*\* |
| 3453 | Battery Fault (Battery Too Cold For Charging)<br>Alarm occurs when the battery temperature is ≤0° C. (32° F.). Charging the battery below this temperature could destroy the battery and damage the unit. During the alarm condition the unit continues to operate using external power and if external power is lost the unit will operate using internal battery power. The soft case should be used because it provides insulation.<br>Mitigation/Info: Battery Too Cold To Charge, Connect External Power, Use Padded Case<br>\*\*Move to Warmer Location\*\* |
| 3455 | Battery Fault - With External Power Connected (Battery Communication Failure)<br>Alarm occurs when the EMV+ is not able to communicate with the internal battery and external power is connected. To continue operation and the unit should remain connected external power.<br>Mitigation/Info: Battery Comm Failure, DO NOT Remove External Power!, Assure Ability to Manually Ventilate Patient<br>\*\*Replace/Service Ventilator\*\* |
| 3470 | Internal Communication (Comm) Failure Fault - PIM Comm<br>Alarm occurs when the EMV+ is not longer able to communicate with the Power Interface Module (PIM). When this occurs the operator should monitor operation continuously, seek to replace the ventilator as soon as possible and assure the ability to manually ventilate the patient.<br>Mitigation/Info: Power Management Failure, Assure Ability To Manually Ventilate Patient, Monitor Power Source<br>\*\*Replace/Service Ventilator\*\* |
| 3480 | SPM Compatibility Fault<br>Alarm occurs when the EMV+ software detects that it has not been calibrated with the SPM that is inside the unit. This fault occurs when the biomedical technician fails to recalibrate the unit following an SPM change or service. When this occurs the unit should be removed from use when appropriate and sent for service.<br>Mitigation/Info: Hardware Compatibility Failure, Update Calibration Records<br>\*\* Replace/Service Ventilator \*\* |

The invention claimed is:

1. A life support and monitoring apparatus for providing ventilation treatment to a patient, the apparatus comprising:
   an oxygen inlet for supplying oxygen from an oxygen source;
   a ventilator module configured to receive and provide at least a portion of the supplied oxygen to the patient via a gas output;
   at least one sensor input for obtaining physiological data from the patient;
   a user interface for communicating alarms, events and/or instructions to a user; and
   a controller associated with a memory and in communication with the ventilator module, the at least one sensor input, and the user interface, the controller configured to:
      perform a self-test on start-up and determine if there are pre-existing fault events,
      receive and process the obtained physiological data from the at least one sensor input,
      control the ventilator module to provide a desired level of inspired oxygen to the patient,
      determine whether multiple fault events have occurred including fault events during operation and the pre-existing fault events and prioritize the multiple fault events based on safety risk to the patient,
      provide, via the user interface, alarms corresponding to the multiple fault events, wherein the alarms are organized according to the prioritization based on safety risk listing higher priority alarms before lower priority alarms, and
      present mitigation information for each alarm for correcting the corresponding fault event,
      wherein at least one of the pre-existing fault events is based on a different parameter than the fault events during operation.

2. The life support and monitoring apparatus according to claim 1, wherein the mitigation information comprises an alarm name and description.

3. The life support and monitoring apparatus according to claim 1, wherein the mitigation information comprises instructions for resolving the corresponding fault event.

4. The life support and monitoring apparatus according to claim 3, wherein the mitigation information further comprises additional guidance if the instructions do not resolve the corresponding fault event.

5. The life support and monitoring apparatus according to claim 1, wherein the mitigation information comprises a service code associated with each alarm.

6. The life support and monitoring apparatus according to claim 1, wherein the mitigation information comprises a visual indication of a severity of the alarm.

7. The life support and monitoring apparatus according to claim 6, wherein the controller is configured to categorize the fault events as high priority, medium priority, or low priority, and wherein the visual indication of the severity of the alarm comprises a visual indication that the fault event is high priority, medium priority, or low priority.

8. The life support and monitoring apparatus according to claim 7, wherein a high priority fault event indicates that mechanical ventilation is no longer possible.

9. The life support and monitoring apparatus according to claim 7, wherein a medium priority fault event indicates that mechanical ventilation is possible, but immediate intervention by an operator is required.

10. The life support and monitoring apparatus according to claim 7, wherein a low priority fault event indicates that mechanical ventilation is possible, but an operator must be aware of the fault event.

11. The life support and monitoring apparatus according to claim 7, wherein the visual indication that the fault event is high priority, medium priority, or low priority comprises a visual display of a high priority icon, a medium priority icon, or a low priority icon.

12. The life support and monitoring apparatus according to claim 1, wherein the user interface comprises a visual display and the mitigation information for each alarm is presented in the visual display, and wherein the user interface allows an operator to scroll through the alarms to view the mitigation information associated with each alarm.

13. The life support and monitoring apparatus according to claim 12, wherein the controller updates the visual display as new fault events have occurred.

14. The life support and monitoring apparatus according to claim 13, wherein the controller resets the visual display to present the mitigation information for a highest priority alarm first.

15. The life support and monitoring apparatus according to claim 1, wherein the user interface provides an audible signal associated with each alarm.

16. The life support and monitoring apparatus according to claim 15, wherein the user interface comprises a mute control to mute the audible signal.

17. The life support and monitoring apparatus according to claim 16, wherein the controller is configured to categorize the fault events as high priority, medium priority, or low priority, and wherein the mute control has no effect on the audible signal for an alarm associated with a high priority fault event, the mute control temporarily mutes the audible signal for a predetermined time period for an alarm associated with a medium priority fault event, and the mute control mutes the audible signal for an alarm associated with a low priority fault event.

18. The life support and monitoring apparatus according to claim 1, wherein the user interface comprises a cancel control to cancel an alarm and a presentation of the mitigation information associated with the alarm.

19. The life support and monitoring apparatus according to claim 1, wherein the controller is configured to adjust the desired level of inspired oxygen based on the obtained physiological data.

20. The life support and monitoring apparatus according to claim 1, wherein the user interface comprises at least one operator control for adjusting at least one parameter limit at which a fault event is determined and a corresponding alarm is provided.

21. The life support and monitoring apparatus according to claim 20, wherein the at least one parameter limit includes at least one of: a heart rate alarm limit, a patient oxygen saturation alarm limit ($SpO_2$), or a peak inspiratory pressure alarm limit.

22. The life support and monitoring apparatus according to claim 1, wherein the mitigation information comprises a visual display of an icon identifying each alarm.

23. The life support and monitoring apparatus according to claim 1, wherein the controller is configured to categorize the fault events as high priority, medium priority, or low priority.

24. The life support and monitoring apparatus according to claim 23, wherein the high priority fault events include at least one of: a compressor failure, a self-check failure, an oxygen ($O_2$) valve failure, a low oxygen ($O_2$) supply pressure, a fresh gas intake failure, a high oxygen ($O_2$) supply pressure, a run-time calibration failure, an airway pressure sensing failure, an exhalation system failure, a required voltage failure, an internal communications failure, an off set self-check failure, a complete power failure, an empty battery level, a display control failure, or a software failure.

25. The life support and monitoring apparatus according to claim 23, wherein the medium priority fault events include at least one of: a compressor fault, an oxygen ($O_2$) valve fault, a low oxygen ($O_2$) supply pressure, a fresh gas intake fault, a sensor calibration failure, an exhalation fault, a high detected airway pressure, a low detected airway pressure, a high detected tidal volume, a low detected tidal volume, a high detected breath rate, a low detected breath rate, a detected pressure leak, a determination that exhaled flow continues throughout an expiratory period, a determination of insufficient flow, a patient disconnect, a pulse oximeter module failure, an internal communications failure, an oxygen saturation ($SpO_2$) sensor disconnect, a low detected patient oxygen saturation ($SpO_2$), a high heart rate detected, a low heart rate detected, an input protection circuit failure, an internal power circuit failure, a low battery level, or a battery fault.

26. The life support and monitoring apparatus according to claim 23, wherein the low priority fault events include at least one of: a compressor fault, an oxygen ($O_2$) valve fault, a fresh gas intake fault, a high oxygen ($O_2$) supply pressure, a battery fault, a self-check fault, an ambient pressure sensor failure, an ambient pressure fault, an operational temperature fault, a self-check fault, a pulse oximeter module shutdown, a pulse oximeter module failure, an oxygen saturation ($SpO_2$) sensor disconnect, an oxygen saturation ($SpO_2$) sensor failure, a pulse oximeter pulse search failure, pulse oximeter signal interference, excessive ambient light, an unrecognized oxygen saturation ($SpO_2$) sensor, a poor oxygen saturation ($SpO_2$) sensor signal, an external power failure or disconnect, a battery disconnect, a low battery level, an external power failure, a battery fault, an internal communications fault, or a software compatibility fault.

27. The life support and monitoring apparatus according to claim 1, wherein the controller is configured to provide, via the user interface, alarms corresponding to the pre-existing fault events.

28. The life support and monitoring apparatus according to claim 27, wherein the controller is configured to categorize the pre-existing fault events as high priority, medium priority, or low priority.

29. The life support and monitoring apparatus according to claim 27, wherein the controller is configured to present mitigation information for each alarm for correcting the corresponding pre-existing fault event, the mitigation information comprising instructions for resolving the corresponding pre-existing fault event.

30. The life support and monitoring apparatus according to claim 1, wherein the controller is configured to begin operation of the ventilator module if the controller determines there are no pre-existing fault events.

* * * * *